US008293516B2

(12) United States Patent
Endo et al.

(10) Patent No.: US 8,293,516 B2
(45) Date of Patent: Oct. 23, 2012

(54) RECOMBINANT MICROORGANISM

(75) Inventors: Keiji Endo, Haga-gun (JP); Katsutoshi Ara, Haga-gun (JP)

(73) Assignee: Kao Corporation, Tokyo (JP)

( * ) Notice: Subject to any disclaimer, the term of this patent is extended or adjusted under 35 U.S.C. 154(b) by 456 days.

(21) Appl. No.: 12/528,039

(22) PCT Filed: Dec. 27, 2007

(86) PCT No.: PCT/JP2007/001481

§ 371 (c)(1), (2), (4) Date: Aug. 20, 2009

(87) PCT Pub. No.: WO2008/102421
PCT Pub. Date: Aug. 28, 2008

(65) Prior Publication Data
US 2010/0255534 A1 Oct. 7, 2010

(30) Foreign Application Priority Data

Feb. 22, 2007 (JP) ................................ 2007-042561

(51) Int. Cl.
*C12N 1/20* (2006.01)
*C12P 21/06* (2006.01)

(52) U.S. Cl. ................................ 435/252.31; 435/69.1

(58) Field of Classification Search ........................ None
See application file for complete search history.

(56) References Cited

U.S. PATENT DOCUMENTS 6,267,966 B1 * 7/2001 Baillie ...................... 424/200.1
6,403,355 B1 6/2002 Hagihara et al.
7,585,674 B2 * 9/2009 Sawada et al. ........... 435/252.31

FOREIGN PATENT DOCUMENTS

JP 04-190793 A 7/1992
JP 2000-184882 A 7/2000
JP 2000-210081 A 8/2000
JP 2006-296242 A 11/2006

OTHER PUBLICATIONS

Kunst, F., et al., "The complete genome sequence of the gram-positive bacterium *Bacillus subtilis,*" *Nature 390*:249-256, Macmillan, United States (1997).

Blattner, F., et al., "The Complete Genome Sequence of *Escherichia coli* K-12," *Science 277*:1453-1462, American Association for the Advancement of Science, United States (1997).

Kontinen, V.P., et al., "The PrsA lipoprotein is essential for protein secretion in *Bacillus subtilis* and sets a limit for high-level secretion," *Mol Microbiol 8*:727-737, Blackwell Scientific Publications, England (1993).

Haima, P. at al. "The effect of restriction on shotgun cloning and plasmid stability in *Bacillus subtilis* Marburg," *Mol Gen Genet 209*:335-342, Springer-Verlag, Germany (1987).

Bron, S., et al., "Stability function in the *Bacillus subtilis* plasmid pTA1060," *Plasmid 18*:8-15, Academic Press, United States (1987).

Strauch, M.A., et al., Transition-state regulators: sentinels of *Bacillus subtilis* post-exponential gene expression, *Mol Microbiol* 7:337-342, Blackwell Scientific Publications, England (1993).

Phillips, Z.E.V., et al., "*Bacillus subtilus* sporulation and stationary phase gene expression," *Cell Mol Life Sci 59*:392-402, Birkhaüser Verlag, Switzerland (2002).

Perego, M., "Incorporation of D-Alanine into Lipoteichoic Acid and Wall Teichoic Acid in *Bacillus subtilus,*" *J. Biol. Chem*.270:15598-15606, The American Society for Biochemistry and Molecular Biology, Inc., United States (1995).

Lahooti, M., et al., "Transcriptional analysis of the *Bacillus subtilis* teichuronic acid operon," *Microbiology 145*:3409-3417, Society for General Microbiology, Great Britain (1999).

Thwaite, J.E., et al., "Optimization of the Cell Wall Microenvironment Allows Increased Production of Recombinant *Bacillus anthracis* Protective Antigen from *B. subtilis,*" *Appl Environ Microbiol* 68:227-234, American Society for Microbiology, United States (2002).

Baillie, L., et al., "The expression of the protective antigen of *Bacillus anthracis* in *Bacillus subtilis,*" *J. Appl. Microbiol*. 64:741-746, The Society for Applied Microbiology, United Kingdom (1998).

Vitikainen, H.-L., et al., "Secretion of heterologous proteins in *Bacillus subtilis* can be improved by engineering cell components affecting post-translocational protein folding and degradation," *J. Appl. Microbiol*. 99:363-375, The Society for Applied Microbiology, United Kingdom (Aug. 2005).

Brigidi, P., et al., "Genetic transformation of intact cells of *Bacillus subtilis* by electroporation," *FEMS Microbiol Lett 67*:135-138, Elsevier Science Publishers, B.V., The Netherlands (1990).

Chang, S., et al., "High frequency transformation of *Bacillus subtilis* protoplasts by plasmid DNA," *J. Mol Gen Genet 168*:111-115, Springer-Verlag, Germany (1979).

Hagihara, H., et al., "Deduced amino-acid sequence of a calcium-free α-amylase from a strain of *Bacillus*: implications from molecular modeling of high oxidation stability and chelator resistance of the enzyme," *Eur J. Biochem 268*:3974-3982, Blackwell Science Ltd., England (2001).

Henrissat B., "A classification of glycosyl hydrolases based on amino acid sequence similarities," *Biochem J. 280*:309-316, Portland Press Ltd., United Kingdom (1991).

(Continued)

*Primary Examiner* — Suzanne M Noakes
*Assistant Examiner* — Jae W Lee
(74) *Attorney, Agent, or Firm* — Sterne, Kessler, Goldstein & Fox P.L.L.C.

(57) ABSTRACT

A recombinant microorganism is provided that has increased productivity of a protein or polypeptide of interest. A method for producing a protein of interest using the microorganism is also provided. The microorganism is prepared by inserting, in its genome, a transcription initiation regulatory region or both a transcription initiation regulatory region and a ribosome-binding site, upstream of a *Bacillus subtilis* prsA gene and by deleting or inactivating one or more of the abrB gene, dltA gene, dltB gene, dltC gene, dltD gene, dltE gene, or a gene (genes) corresponding thereto.

11 Claims, 5 Drawing Sheets

OTHER PUBLICATIONS

Hoch, J.A., et al., "Transformation and Transduction in Recombination-defective Mutants of *Bacillus subtilis*," *J. Bacteriol* 93:1925-1937, American Society for Microbiology, United States (1967).

Horton, R.M., et al., "Engineering hybrid genes without the use of restriction enzymes: gene splicing by overlap extension," *Gene* 77:61-68, Elsevier Science Publishers, B.V., The Netherlands (1989).

Itaya, M., et al., "Gene-directed mutagenesis on the chromosome of *Bacillus subtilis* 168," *J. Mol Gen Genet* 223:268-272, Springer-Verlag, Germany (1990).

Lipman, D.J., et al., "Rapid and Sensitive Protein Similarity Searches," *Science* 227:1435-1441, American Association for the Advancement of Science, United States (1985).

Shine, J., et al., "The 3'-Terminal Sequence of *Escherichia coli* 16S Ribosomal RNA: Complementarity to Nonsense Triplets and Ribosome Binding Sites," *Proc Natl Acad Sci USA* 71:1342-1346, United States (1974).

International Search Report mailed Feb. 5, 2008, for PCT/JP2007/001481, Japanese Patent Office, Tokyo, Japan.

* cited by examiner

SEQUENCE LISTING

```
<160> NUMBER OF SEQ ID NOS: 56

<210> SEQ ID NO 1
<211> LENGTH: 1740
<212> TYPE: DNA
<213> ORGANISM: Bacillus subtilis
<220> FEATURE:
<221> NAME/KEY: CDS
<222> LOCATION: (811)..(1689)

<400> SEQUENCE: 1
ttgaaaagta gtcaaaccct ggtgctggtg gcgattttc aatttgcatt ctatcttttt      60
taataaatat ttggtaatgt aatatgggac agttcagaga gaggggggaat ctcccatcat    120 tttattctat tttatcgtgg ctgccgtgtt tattttatat ttcataaaca ggctcaccaa    180
tacattatgc cttgtcagag agattcctga agagcggcaa gataaggtat tccgatttat    240
taatgtatct atattaattt tactgatctc ttcgtttgtg gagatctcct ttacagtgta    300
aatacgaaag aaagcatagc tgctgattaa gcagctatgc tttttttatgt tgattagtac    360 agccaagaag cgccgatgat aatcaataaa ataaataaca caaccaataa agcgaatccg    420
cctgcaaata cttcacccat cttaaatagc acctcctgta ataagcttta tttaccaatt    480
acatgttatg caattcatgt ttgaaacgat taggcgctag tgaaaataaa ggatcgctta    540
tgttgcaagc gatcctcggg ctgcttagta gatgtaagct gcacctacga tgataagcaa    600
aatgaacagt actacgagca acgcgaatcc gttagagtat cctccgctca tgttacatac    660
ctccttttct tgatcaatat ataagtatgt catcagcaaa agtttgacta gacgaatgcc    720
ctttatttaa aatcttttta cagaaagcca caatatgtta tgatacgcat aggtaattta    780
atttggaatg attaggagtg tttgaaaaca atg aag aaa atc gca ata gca gct    834
                                   Met Lys Lys Ile Ala Ile Ala Ala
                                     1               5 atc act gct aca agc atc ctc gct ctc agt gct tgc agc agc ggc gac    882
Ile Thr Ala Thr Ser Ile Leu Ala Leu Ser Ala Cys Ser Ser Gly Asp
       10                  15                  20 aaa gaa gtt atc gca aaa aca gac gca ggc gat gtc aca aaa ggc gag    930
Lys Glu Val Ile Ala Lys Thr Asp Ala Gly Asp Val Thr Lys Gly Glu
 25                  30                  35                  40 ctt tac aca aac atg aag aaa aca gct ggc gca agc gta ctg aca cag    978
Leu Tyr Thr Asn Met Lys Lys Thr Ala Gly Ala Ser Val Leu Thr Gln
                     45                  50                  55 cta gtg caa gaa aaa gta ttg gac aag aag tat aaa gtt tcg gat aaa   1026
Leu Val Gln Glu Lys Val Leu Asp Lys Lys Tyr Lys Val Ser Asp Lys
             60                  65                  70
```

```
gaa att gac aac aag ctg aaa gaa tac aaa acg cag ctt ggc gat caa    1074
Glu Ile Asp Asn Lys Leu Lys Glu Tyr Lys Thr Gln Leu Gly Asp Gln
            75                  80                  85 tat act gcc ctc gaa aag caa tat ggc aaa gat tac ctg aaa gaa caa    1122
Tyr Thr Ala Leu Glu Lys Gln Tyr Gly Lys Asp Tyr Leu Lys Glu Gln
         90                  95                 100 gta aaa tat gaa ttg ctg aca caa aaa gcg gct aaa gat aac atc aaa    1170
Val Lys Tyr Glu Leu Leu Thr Gln Lys Ala Ala Lys Asp Asn Ile Lys
105                 110                 115                 120 gta aca gac gcc gat atc aaa gag tac tgg gaa ggc tta aaa ggc aaa    1218
Val Thr Asp Ala Asp Ile Lys Glu Tyr Trp Glu Gly Leu Lys Gly Lys
                125                 130                 135 atc cgt gca agc cac atc ctt gtt gct gat aaa aag aca gct gaa gaa    1266
Ile Arg Ala Ser His Ile Leu Val Ala Asp Lys Lys Thr Ala Glu Glu
            140                 145                 150 gta gag aaa aag ctg aaa aaa ggc gag aag ttt gaa gac ctt gcg aaa    1314
Val Glu Lys Lys Leu Lys Lys Gly Glu Lys Phe Glu Asp Leu Ala Lys
        155                 160                 165 gaa tac tca aca gac agc tct gct tca aaa ggc ggg gat ctt ggc tgg    1362
Glu Tyr Ser Thr Asp Ser Ser Ala Ser Lys Gly Gly Asp Leu Gly Trp
    170                 175                 180 ttc gca aaa gaa ggc caa atg gac gaa aca ttc agc aaa gct gca ttc    1410
Phe Ala Lys Glu Gly Gln Met Asp Glu Thr Phe Ser Lys Ala Ala Phe
185                 190                 195                 200 aaa tta aaa aca ggt gaa gtc agt gat cct gtc aaa acg caa tac ggc    1458
Lys Leu Lys Thr Gly Glu Val Ser Asp Pro Val Lys Thr Gln Tyr Gly
            205                 210                 215 tac cat atc att aaa aag aca gaa gaa cgc ggc aaa tat gat gat atg    1506
Tyr His Ile Ile Lys Lys Thr Glu Glu Arg Gly Lys Tyr Asp Asp Met
        220                 225                 230 aaa aaa gaa ctg aaa tct gaa gtg ctt gaa caa aaa tta aat gac aac    1554
Lys Lys Glu Leu Lys Ser Glu Val Leu Glu Gln Lys Leu Asn Asp Asn
    235                 240                 245 gca gct gtt cag gaa gct gtt caa aaa gtc atg aag aag gct gac atc    1602
Ala Ala Val Gln Glu Ala Val Gln Lys Val Met Lys Lys Ala Asp Ile
250                 255                 260 gaa gta aaa gat aaa gat ctg aaa gac aca ttt aat aca tct tca aca    1650
Glu Val Lys Asp Lys Asp Leu Lys Asp Thr Phe Asn Thr Ser Ser Thr
265                 270                 275                 280 agc aac agc act tct tca tct tca agc aat tct aaa taa taaaaaagc     1699
Ser Asn Ser Thr Ser Ser Ser Ser Asn Ser Lys
            285                 290 tgtgcggctc attgagccgc acagctttt ttatgcgatg g                     1740
```

<210> SEQ ID NO 2
<211> LENGTH: 292
<212> TYPE: PRT
<213> ORGANISM: Bacillus subtilis

<400> SEQUENCE: 2

```
Met Lys Lys Ile Ala Ile Ala Ala Ile Thr Ala Thr Ser Ile Leu Ala
1               5                   10                  15

Leu Ser Ala Cys Ser Ser Gly Asp Lys Glu Val Ile Ala Lys Thr Asp
            20                  25                  30

Ala Gly Asp Val Thr Lys Gly Glu Leu Tyr Thr Asn Met Lys Lys Thr
        35                  40                  45

Ala Gly Ala Ser Val Leu Thr Gln Leu Val Gln Glu Lys Val Leu Asp
    50                  55                  60

Lys Lys Tyr Lys Val Ser Asp Lys Glu Ile Asp Asn Lys Leu Lys Glu
65                  70                  75                  80
```

```
Tyr Lys Thr Gln Leu Gly Asp Gln Tyr Thr Ala Leu Glu Lys Gln Tyr
                85                  90                  95

Gly Lys Asp Tyr Leu Lys Glu Gln Val Lys Tyr Glu Leu Leu Thr Gln
            100                 105                 110

Lys Ala Ala Lys Asp Asn Ile Lys Val Thr Asp Ala Asp Ile Lys Glu
        115                 120                 125

Tyr Trp Glu Gly Leu Lys Gly Lys Ile Arg Ala Ser His Ile Leu Val
130                 135                 140

Ala Asp Lys Lys Thr Ala Glu Glu Val Glu Lys Lys Leu Lys Lys Gly
145                 150                 155                 160

Glu Lys Phe Glu Asp Leu Ala Lys Glu Tyr Ser Thr Asp Ser Ser Ala
                165                 170                 175

Ser Lys Gly Gly Asp Leu Gly Trp Phe Ala Lys Glu Gly Gln Met Asp
            180                 185                 190

Glu Thr Phe Ser Lys Ala Ala Phe Lys Leu Lys Thr Gly Glu Val Ser
        195                 200                 205

Asp Pro Val Lys Thr Gln Tyr Gly Tyr His Ile Ile Lys Lys Thr Glu
210                 215                 220

Glu Arg Gly Lys Tyr Asp Asp Met Lys Lys Glu Leu Lys Ser Glu Val
225                 230                 235                 240

Leu Glu Gln Lys Leu Asn Asp Asn Ala Ala Val Gln Glu Ala Val Gln
                245                 250                 255

Lys Val Met Lys Lys Ala Asp Ile Glu Val Lys Asp Lys Asp Leu Lys
            260                 265                 270

Asp Thr Phe Asn Thr Ser Ser Thr Ser Asn Ser Thr Ser Ser Ser Ser
        275                 280                 285

Ser Asn Ser Lys
    290

<210> SEQ ID NO 3
<211> LENGTH: 1531
<212> TYPE: DNA
<213> ORGANISM: Unknown
<220> FEATURE:
<223> OTHER INFORMATION: Bacillus sp. KSM-K38
<220> FEATURE:
<221> NAME/KEY: CDS
<222> LOCATION: (1)..(1440)

<400> SEQUENCE: 3 gat gga ttg aac ggt acg atg atg cag tat tat gag tgg cat ttg gaa      48
Asp Gly Leu Asn Gly Thr Met Met Gln Tyr Tyr Glu Trp His Leu Glu
1               5                   10                  15 aac gac ggg cag cat tgg aat cgg ttg cac gat gat gcc gca gct ttg      96
Asn Asp Gly Gln His Trp Asn Arg Leu His Asp Asp Ala Ala Ala Leu
            20                  25                  30 agt gat gct ggt att aca gct att tgg att ccg cca gcc tac aaa ggt     144
Ser Asp Ala Gly Ile Thr Ala Ile Trp Ile Pro Pro Ala Tyr Lys Gly
        35                  40                  45 aat agt cag gcg gat gtt ggg tac ggt gca tac gat ctt tat gat tta     192
Asn Ser Gln Ala Asp Val Gly Tyr Gly Ala Tyr Asp Leu Tyr Asp Leu
    50                  55                  60 gga gag ttc aat caa aag ggt act gtt cga acg aaa tac gga act aag     240
Gly Glu Phe Asn Gln Lys Gly Thr Val Arg Thr Lys Tyr Gly Thr Lys
65                  70                  75                  80 gca cag ctt gaa cga gct att ggg tcc ctt aaa tct aat gat atc aat     288
Ala Gln Leu Glu Arg Ala Ile Gly Ser Leu Lys Ser Asn Asp Ile Asn
                85                  90                  95
```

```
                                                  -continued
gta tac gga gat gtc gtg atg aat cat aaa atg gga gct gat ttt acg        336
Val Tyr Gly Asp Val Val Met Asn His Lys Met Gly Ala Asp Phe Thr
        100                 105                 110 gag gca gtg caa gct gtt caa gta aat cca acg aat cgt tgg cag gat        384
Glu Ala Val Gln Ala Val Gln Val Asn Pro Thr Asn Arg Trp Gln Asp
    115                 120                 125 att tca ggt gcc tac acg att gat gcg tgg acg ggt ttc gac ttt tca        432
Ile Ser Gly Ala Tyr Thr Ile Asp Ala Trp Thr Gly Phe Asp Phe Ser
130                 135                 140 ggg cgt aac aac gcc tat tca gat ttt aag tgg aga tgg ttc cat ttt        480
Gly Arg Asn Asn Ala Tyr Ser Asp Phe Lys Trp Arg Trp Phe His Phe
145                 150                 155                 160 aat ggt gtt gac tgg gat cag cgc tat caa gaa aat cat att ttc cgc        528
Asn Gly Val Asp Trp Asp Gln Arg Tyr Gln Glu Asn His Ile Phe Arg
            165                 170                 175 ttt gca aat acg aac tgg aac tgg cga gtg gat gaa gag aac ggt aat        576
Phe Ala Asn Thr Asn Trp Asn Trp Arg Val Asp Glu Glu Asn Gly Asn
        180                 185                 190 tat gat tac ctg tta gga tcg aat atc gac ttt agt cat cca gaa gta        624
Tyr Asp Tyr Leu Leu Gly Ser Asn Ile Asp Phe Ser His Pro Glu Val
    195                 200                 205 caa gat gag ttg aag gat tgg ggt agc tgg ttt acc gat gag tta gat        672
Gln Asp Glu Leu Lys Asp Trp Gly Ser Trp Phe Thr Asp Glu Leu Asp
210                 215                 220 ttg gat ggt tat cgt tta gat gct att aaa cat att cca ttc tgg tat        720
Leu Asp Gly Tyr Arg Leu Asp Ala Ile Lys His Ile Pro Phe Trp Tyr
225                 230                 235                 240 aca tct gat tgg gtt cgg cat cag cgc aac gaa gca gat caa gat tta        768
Thr Ser Asp Trp Val Arg His Gln Arg Asn Glu Ala Asp Gln Asp Leu
            245                 250                 255 ttt gtc gta ggg gaa tat tgg aag gat gac gta ggt gct ctc gaa ttt        816
Phe Val Val Gly Glu Tyr Trp Lys Asp Asp Val Gly Ala Leu Glu Phe
        260                 265                 270 tat tta gat gaa atg aat tgg gag atg tct cta ttc gat gtt cca ctt        864
Tyr Leu Asp Glu Met Asn Trp Glu Met Ser Leu Phe Asp Val Pro Leu
    275                 280                 285 aat tat aat ttt tac cgg gct tca caa caa ggt gga agc tat gat atg        912
Asn Tyr Asn Phe Tyr Arg Ala Ser Gln Gln Gly Gly Ser Tyr Asp Met
290                 295                 300 cgt aat att tta cga gga tct tta gta gaa gcg cat ccg atg cat gca        960
Arg Asn Ile Leu Arg Gly Ser Leu Val Glu Ala His Pro Met His Ala
305                 310                 315                 320 gtt acg ttt gtt gat aat cat gat act cag cca ggg gag tca tta gag       1008
Val Thr Phe Val Asp Asn His Asp Thr Gln Pro Gly Glu Ser Leu Glu
            325                 330                 335 tca tgg gtt gct gat tgg ttt aag cca ctt gct tat gcg aca att ttg       1056
Ser Trp Val Ala Asp Trp Phe Lys Pro Leu Ala Tyr Ala Thr Ile Leu
        340                 345                 350 acg cgt gaa ggt ggt tat cca aat gta ttt tac ggt gat tac tat ggg       1104
Thr Arg Glu Gly Gly Tyr Pro Asn Val Phe Tyr Gly Asp Tyr Tyr Gly
    355                 360                 365 att cct aac gat aac att tca gct aaa aaa gat atg att gat gag ctg       1152
Ile Pro Asn Asp Asn Ile Ser Ala Lys Lys Asp Met Ile Asp Glu Leu
370                 375                 380 ctt gat gca cgt caa aat tac gca tat ggc acg cag cat gac tat ttt       1200
Leu Asp Ala Arg Gln Asn Tyr Ala Tyr Gly Thr Gln His Asp Tyr Phe
385                 390                 395                 400 gat cat tgg gat gtt gta gga tgg act agg gaa gga tct tcc tcc aga       1248
Asp His Trp Asp Val Val Gly Trp Thr Arg Glu Gly Ser Ser Ser Arg
            405                 410                 415
```

```
                                              -continued
cct aat tca ggc ctt gcg act att atg tcg aat gga cct ggt ggt tcc    1296
Pro Asn Ser Gly Leu Ala Thr Ile Met Ser Asn Gly Pro Gly Gly Ser
        420                 425                 430 aag tgg atg tat gta gga cgt cag aat gca gga caa aca tgg aca gat    1344
Lys Trp Met Tyr Val Gly Arg Gln Asn Ala Gly Gln Thr Trp Thr Asp
        435                 440                 445 tta act ggt aat aac gga gcg tcc gtt aca att aat ggc gat gga tgg    1392
Leu Thr Gly Asn Asn Gly Ala Ser Val Thr Ile Asn Gly Asp Gly Trp
        450                 455                 460 ggc gaa ttc ttt acg aat gga gga tct gta tcc gtg tac gtg aac caa    1440
Gly Glu Phe Phe Thr Asn Gly Gly Ser Val Ser Val Tyr Val Asn Gln
465                 470                 475                 480 taacaaaaag ccttgagaag ggattcctcc ctaactcaag ctttcttta tgtcgcttag    1500 ctttacgctt ctacgacttt gaagcttggg g                                 1531

<210> SEQ ID NO 4
<211> LENGTH: 480
<212> TYPE: PRT
<213> ORGANISM: Unknown
<220> FEATURE:
<223> OTHER INFORMATION: Bacillus sp. KSM-K38

<400> SEQUENCE: 4

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270
```

```
Tyr Leu Asp Glu Met Asn Trp Glu Met Ser Leu Phe Asp Val Pro Leu
            275                 280                 285

Asn Tyr Asn Phe Tyr Arg Ala Ser Gln Gln Gly Ser Tyr Asp Met
        290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
        370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 5
<211> LENGTH: 3150
<212> TYPE: DNA
<213> ORGANISM: Unknown
<220> FEATURE:
<223> OTHER INFORMATION: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 5
gatttgccga tgcaacaggc ttatatttag aggaaatttc ttttttaaatt gaatacggaa    60 taaaatcagg taaacaggtc ctgatttat ttttttgagt ttttttagaga actgaagatt   120 gaaataaaag tagaagacaa aggacataag aaaattgcat tagttttaat tatagaaaac   180
gcctttttat aattatttat acctagaacg aaaatactgt ttcgaaagcg gtttactata   240
aaaccttata ttccggctct tttttaaaac aggggggtaaa aattcactct agtattctaa   300
tttcaacatg ctataataaa tttgtaagac gcaatatgca tctcttttt tacgatatat   360 gtaagcggtt aaccttgtgc tatatgccga tttaggaagg ggggtagatt gagtcaagta   420
gtaataatat agataactta taagttgttg agaagcagga gagcatctgg ttactcaca    480 agtttttta aaactttaac gaaagcactt tcggtaatgc ttatgaattt agctatttga    540
ttcaattact ttaaaaatat ttaggaggta at atg atg tta aga aag aaa aca    593
                                   Met Met Leu Arg Lys Lys Thr
                                   -25
```

| | | | | | | | | | | | | | | | | |
|---|---|---|---|---|---|---|---|---|---|---|---|---|---|---|---|---|
| aag | cag | ttg | att | tct | tcc | att | ctt | att | tta | gtt | tta | ctt | cta | tct | tta | 641 |
| Lys | Gln | Leu | Ile | Ser | Ser | Ile | Leu | Ile | Leu | Val | Leu | Leu | Leu | Ser | Leu | |
| | | -20 | | | | -15 | | | | -10 | | | | | | |
| ttt | ccg | gca | gct | ctt | gca | gca | gaa | gga | aac | act | cgt | gaa | gac | aat | ttt | 689 |
| Phe | Pro | Ala | Ala | Leu | Ala | Ala | Glu | Gly | Asn | Thr | Arg | Glu | Asp | Asn | Phe | |
| | -5 | | | | -1 | 1 | | | | 5 | | | | | 10 | |
| aaa | cat | tta | tta | ggt | aat | gac | aat | gtt | aaa | cgc | cct | tct | gag | gct | ggc | 737 |
| Lys | His | Leu | Leu | Gly | Asn | Asp | Asn | Val | Lys | Arg | Pro | Ser | Glu | Ala | Gly | |
| | | | | 15 | | | | | 20 | | | | | 25 | | |
| gca | tta | caa | tta | caa | gaa | gtc | gat | gga | caa | atg | aca | tta | gta | gat | caa | 785 |
| Ala | Leu | Gln | Leu | Gln | Glu | Val | Asp | Gly | Gln | Met | Thr | Leu | Val | Asp | Gln | |
| | | | 30 | | | | | 35 | | | | | 40 | | | |
| cat | gga | gaa | aaa | att | caa | tta | cgt | gga | atg | agt | aca | cac | gga | tta | cag | 833 |
| His | Gly | Glu | Lys | Ile | Gln | Leu | Arg | Gly | Met | Ser | Thr | His | Gly | Leu | Gln | |
| | | | 45 | | | | | 50 | | | | | 55 | | | |
| tgg | ttt | cct | gag | atc | ttg | aat | gat | aac | gca | tac | aaa | gct | ctt | tct | aac | 881 |
| Trp | Phe | Pro | Glu | Ile | Leu | Asn | Asp | Asn | Ala | Tyr | Lys | Ala | Leu | Ser | Asn | |
| | 60 | | | | | 65 | | | | | 70 | | | | | |
| gat | tgg | gat | tcc | aat | atg | att | cgt | ctt | gct | atg | tat | gta | ggt | gaa | aat | 929 |
| Asp | Trp | Asp | Ser | Asn | Met | Ile | Arg | Leu | Ala | Met | Tyr | Val | Gly | Glu | Asn | |
| 75 | | | | | 80 | | | | | 85 | | | | | 90 | |
| ggg | tac | gct | aca | aac | cct | gag | tta | atc | aaa | caa | aga | gtg | att | gat | gga | 977 |
| Gly | Tyr | Ala | Thr | Asn | Pro | Glu | Leu | Ile | Lys | Gln | Arg | Val | Ile | Asp | Gly | |
| | | | | 95 | | | | | 100 | | | | | 105 | | |
| att | gag | tta | gcg | att | gaa | aat | gac | atg | tat | gtt | att | gtt | gac | tgg | cat | 1025 |
| Ile | Glu | Leu | Ala | Ile | Glu | Asn | Asp | Met | Tyr | Val | Ile | Val | Asp | Trp | His | |
| | | | 110 | | | | | 115 | | | | | 120 | | | |
| gtt | cat | gcg | cca | ggt | gat | cct | aga | gat | cct | gtt | tat | gca | ggt | gct | aaa | 1073 |
| Val | His | Ala | Pro | Gly | Asp | Pro | Arg | Asp | Pro | Val | Tyr | Ala | Gly | Ala | Lys | |
| | | 125 | | | | | 130 | | | | | 135 | | | | |
| gat | ttc | ttt | aga | gaa | att | gca | gct | tta | tac | cct | aat | aat | cca | cac | att | 1121 |
| Asp | Phe | Phe | Arg | Glu | Ile | Ala | Ala | Leu | Tyr | Pro | Asn | Asn | Pro | His | Ile | |
| | 140 | | | | | 145 | | | | | 150 | | | | | |
| att | tat | gag | tta | gcg | aat | gag | ccg | agt | agt | aat | aat | aat | ggt | gga | gca | 1169 |
| Ile | Tyr | Glu | Leu | Ala | Asn | Glu | Pro | Ser | Ser | Asn | Asn | Asn | Gly | Gly | Ala | |
| 155 | | | | | 160 | | | | | 165 | | | | | 170 | |
| ggg | att | ccg | aat | aac | gaa | gaa | ggt | tgg | aaa | gcg | gta | aaa | gaa | tat | gct | 1217 |
| Gly | Ile | Pro | Asn | Asn | Glu | Glu | Gly | Trp | Lys | Ala | Val | Lys | Glu | Tyr | Ala | |
| | | | | 175 | | | | | 180 | | | | | 185 | | |
| gat | cca | att | gta | gaa | atg | tta | cgt | aaa | agc | ggt | aat | gca | gat | gac | aac | 1265 |
| Asp | Pro | Ile | Val | Glu | Met | Leu | Arg | Lys | Ser | Gly | Asn | Ala | Asp | Asp | Asn | |
| | | | 190 | | | | | 195 | | | | | 200 | | | |
| att | atc | att | gtt | ggt | agt | cca | aac | tgg | agt | cag | cgt | ccg | gac | tta | gca | 1313 |
| Ile | Ile | Ile | Val | Gly | Ser | Pro | Asn | Trp | Ser | Gln | Arg | Pro | Asp | Leu | Ala | |
| | | 205 | | | | | 210 | | | | | 215 | | | | |
| gct | gat | aat | cca | att | gat | gat | cac | cat | aca | atg | tat | act | gtt | cac | ttc | 1361 |
| Ala | Asp | Asn | Pro | Ile | Asp | Asp | His | His | Thr | Met | Tyr | Thr | Val | His | Phe | |
| | 220 | | | | | 225 | | | | | 230 | | | | | |
| tac | act | ggt | tca | cat | gct | gct | tca | act | gaa | agc | tat | ccg | tct | gaa | act | 1409 |
| Tyr | Thr | Gly | Ser | His | Ala | Ala | Ser | Thr | Glu | Ser | Tyr | Pro | Ser | Glu | Thr | |
| 235 | | | | | 240 | | | | | 245 | | | | | 250 | |
| cct | aac | tct | gaa | aga | gga | aac | gta | atg | agt | aac | act | cgt | tat | gcg | tta | 1457 |
| Pro | Asn | Ser | Glu | Arg | Gly | Asn | Val | Met | Ser | Asn | Thr | Arg | Tyr | Ala | Leu | |
| | | | | 255 | | | | | 260 | | | | | 265 | | |
| gaa | aac | gga | gta | gcg | gta | ttt | gca | aca | gag | tgg | gga | acg | agt | caa | gct | 1505 |
| Glu | Asn | Gly | Val | Ala | Val | Phe | Ala | Thr | Glu | Trp | Gly | Thr | Ser | Gln | Ala | |
| | | | 270 | | | | | 275 | | | | | 280 | | | |
| agt | gga | gac | ggt | ggt | cct | tac | ttt | gat | gaa | gca | gat | gta | tgg | att | gaa | 1553 |
| Ser | Gly | Asp | Gly | Gly | Pro | Tyr | Phe | Asp | Glu | Ala | Asp | Val | Trp | Ile | Glu | |
| | 285 | | | | | 290 | | | | | 295 | | | | | |

| | | | | | | | | | | | | | | | | |
|---|---|---|---|---|---|---|---|---|---|---|---|---|---|---|---|---|
| ttt | tta | aat | gaa | aac | aac | att | agc | tgg | gct | aac | tgg | tct | tta | acg | aat | 1601 |
| Phe | Leu | Asn | Glu | Asn | Asn | Ile | Ser | Trp | Ala | Asn | Trp | Ser | Leu | Thr | Asn | |
| | | 300 | | | | | 305 | | | | 310 | | | | | |
| aaa | aat | gaa | gta | tct | ggt | gca | ttt | aca | cca | ttc | gag | tta | ggt | aag | tct | 1649 |
| Lys | Asn | Glu | Val | Ser | Gly | Ala | Phe | Thr | Pro | Phe | Glu | Leu | Gly | Lys | Ser | |
| 315 | | | | 320 | | | | | 325 | | | | | 330 | | |
| aac | gca | acc | aat | ctt | gac | cca | ggt | cca | gat | cat | gtg | tgg | gca | cca | gaa | 1697 |
| Asn | Ala | Thr | Asn | Leu | Asp | Pro | Gly | Pro | Asp | His | Val | Trp | Ala | Pro | Glu | |
| | | | 335 | | | | | 340 | | | | | 345 | | | |
| gaa | tta | agt | ctt | tct | gga | gaa | tat | gta | cgt | gct | cgt | att | aaa | ggt | gtg | 1745 |
| Glu | Leu | Ser | Leu | Ser | Gly | Glu | Tyr | Val | Arg | Ala | Arg | Ile | Lys | Gly | Val | |
| | | 350 | | | | | 355 | | | | | 360 | | | | |
| aac | tat | gag | cca | atc | gac | cgt | aca | aaa | tac | acg | aaa | gta | ctt | tgg | gac | 1793 |
| Asn | Tyr | Glu | Pro | Ile | Asp | Arg | Thr | Lys | Tyr | Thr | Lys | Val | Leu | Trp | Asp | |
| | | 365 | | | | | 370 | | | | | 375 | | | | |
| ttt | aat | gat | gga | acg | aag | caa | gga | ttt | gga | gtg | aat | tcg | gat | tct | cca | 1841 |
| Phe | Asn | Asp | Gly | Thr | Lys | Gln | Gly | Phe | Gly | Val | Asn | Ser | Asp | Ser | Pro | |
| | 380 | | | | | 385 | | | | | 390 | | | | | |
| aat | aaa | gaa | ctt | att | gca | gtt | gat | aat | gaa | aac | aac | act | ttg | aaa | gtt | 1889 |
| Asn | Lys | Glu | Leu | Ile | Ala | Val | Asp | Asn | Glu | Asn | Asn | Thr | Leu | Lys | Val | |
| 395 | | | | | 400 | | | | | 405 | | | | | 410 | |
| tcg | gga | tta | gat | gta | agt | aac | gat | gtt | tca | gat | ggc | aac | ttc | tgg | gct | 1937 |
| Ser | Gly | Leu | Asp | Val | Ser | Asn | Asp | Val | Ser | Asp | Gly | Asn | Phe | Trp | Ala | |
| | | | | 415 | | | | | 420 | | | | | 425 | | |
| aat | gct | cgt | ctt | tct | gcc | aac | ggt | tgg | gga | aaa | agt | gtt | gat | att | tta | 1985 |
| Asn | Ala | Arg | Leu | Ser | Ala | Asn | Gly | Trp | Gly | Lys | Ser | Val | Asp | Ile | Leu | |
| | | | 430 | | | | | 435 | | | | | 440 | | | |
| ggt | gct | gag | aag | ctt | aca | atg | gat | gtt | att | gtt | gat | gaa | cca | acg | acg | 2033 |
| Gly | Ala | Glu | Lys | Leu | Thr | Met | Asp | Val | Ile | Val | Asp | Glu | Pro | Thr | Thr | |
| | | | 445 | | | | | 450 | | | | | 455 | | | |
| gta | gct | att | gcg | gcg | att | cca | caa | agt | agt | aaa | agt | gga | tgg | gca | aat | 2081 |
| Val | Ala | Ile | Ala | Ala | Ile | Pro | Gln | Ser | Ser | Lys | Ser | Gly | Trp | Ala | Asn | |
| | 460 | | | | | 465 | | | | | 470 | | | | | |
| cca | gag | cgt | gct | gtt | cga | gtg | aac | gcg | gaa | gat | ttt | gtc | cag | caa | acg | 2129 |
| Pro | Glu | Arg | Ala | Val | Arg | Val | Asn | Ala | Glu | Asp | Phe | Val | Gln | Gln | Thr | |
| 475 | | | | | 480 | | | | | 485 | | | | | 490 | |
| gac | ggt | aag | tat | aaa | gct | gga | tta | aca | att | aca | gga | gaa | gat | gct | cct | 2177 |
| Asp | Gly | Lys | Tyr | Lys | Ala | Gly | Leu | Thr | Ile | Thr | Gly | Glu | Asp | Ala | Pro | |
| | | | | 495 | | | | | 500 | | | | | 505 | | |
| aac | cta | aaa | aat | atc | gct | ttt | cat | gaa | gaa | gat | aac | aat | atg | aac | aac | 2225 |
| Asn | Leu | Lys | Asn | Ile | Ala | Phe | His | Glu | Glu | Asp | Asn | Asn | Met | Asn | Asn | |
| | | | 510 | | | | | 515 | | | | | 520 | | | |
| atc | att | ctg | ttc | gtg | gga | act | gat | gca | gct | gac | gtt | att | tac | tta | gat | 2273 |
| Ile | Ile | Leu | Phe | Val | Gly | Thr | Asp | Ala | Ala | Asp | Val | Ile | Tyr | Leu | Asp | |
| | | 525 | | | | | 530 | | | | | 535 | | | | |
| aac | att | aaa | gta | att | gga | aca | gaa | gtt | gaa | att | cca | gtt | gtt | cat | gat | 2321 |
| Asn | Ile | Lys | Val | Ile | Gly | Thr | Glu | Val | Glu | Ile | Pro | Val | Val | His | Asp | |
| | 540 | | | | | 545 | | | | | 550 | | | | | |
| cca | aaa | gga | gaa | gct | gtt | ctt | cct | tct | gtt | ttt | gaa | gac | ggt | aca | cgt | 2369 |
| Pro | Lys | Gly | Glu | Ala | Val | Leu | Pro | Ser | Val | Phe | Glu | Asp | Gly | Thr | Arg | |
| 555 | | | | | 560 | | | | | 565 | | | | | 570 | |
| caa | ggt | tgg | gac | tgg | gct | gga | gag | tct | ggt | gtg | aaa | aca | gct | tta | aca | 2417 |
| Gln | Gly | Trp | Asp | Trp | Ala | Gly | Glu | Ser | Gly | Val | Lys | Thr | Ala | Leu | Thr | |
| | | | | 575 | | | | | 580 | | | | | 585 | | |
| att | gaa | gaa | gca | aac | ggt | tct | aac | gcg | tta | tca | tgg | gaa | ttt | gga | tat | 2465 |
| Ile | Glu | Glu | Ala | Asn | Gly | Ser | Asn | Ala | Leu | Ser | Trp | Glu | Phe | Gly | Tyr | |
| | | | | 590 | | | | | 595 | | | | | 600 | | |
| cca | gaa | gta | aaa | cct | agt | gat | aac | tgg | gca | aca | gct | cca | cgt | tta | gat | 2513 |
| Pro | Glu | Val | Lys | Pro | Ser | Asp | Asn | Trp | Ala | Thr | Ala | Pro | Arg | Leu | Asp | |
| | | 605 | | | | | 610 | | | | | 615 | | | | |

```
ttc tgg aaa tct gac ttg gtt cgc ggt gag aat gat tat gta gct ttt    2561
Phe Trp Lys Ser Asp Leu Val Arg Gly Glu Asn Asp Tyr Val Ala Phe
            620                 625                 630 gat ttc tat cta gat cca gtt cgt gca aca gaa ggc gca atg aat atc    2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca    2657
Asn Leu Val Phe Gln Pro Pro Thr Asn Gly Tyr Trp Val Gln Ala Pro
                655                 660                 665 aaa acg tat acg att aac ttt gat gaa tta gag gaa gcg aat caa gta    2705
Lys Thr Tyr Thr Ile Asn Phe Asp Glu Leu Glu Glu Ala Asn Gln Val
            670                 675                 680 aat ggt tta tat cac tat gaa gtg aaa att aac gta aga gat att aca    2753
Asn Gly Leu Tyr His Tyr Glu Val Lys Ile Asn Val Arg Asp Ile Thr
        685                 690                 695 aac att caa gat gac acg tta cta cgt aac atg atg atc att ttt gca    2801
Asn Ile Gln Asp Asp Thr Leu Leu Arg Asn Met Met Ile Ile Phe Ala
700                 705                 710 gat gta gaa agt gac ttt gca ggg aga gtc ttt gta gat aat gtt cgt    2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat    2897
Phe Glu Gly Ala Ala Thr Thr Glu Pro Val Glu Pro Glu Pro Val Asp
                735                 740                 745 cct ggc gaa gag acg cca cct gtc gat gag aag gaa gcg aaa aaa gaa    2945
Pro Gly Glu Glu Thr Pro Pro Val Asp Glu Lys Glu Ala Lys Lys Glu
            750                 755                 760 caa aaa gaa gca gag aaa gaa gag aaa gaa gca gta aaa gaa gaa aag    2993
Gln Lys Glu Ala Glu Lys Glu Glu Lys Glu Ala Val Lys Glu Glu Lys
        765                 770                 775 aaa gaa gct aaa gaa gaa aag aaa gca gtc aaa aat gag gct aag aaa    3041
Lys Glu Ala Lys Glu Glu Lys Lys Ala Val Lys Asn Glu Ala Lys Lys
780                 785                 790 aaa   taatctatta aactagttat agggttatct aaaggtctga tgtagatctt       3094
Lys
795 ttagataacc ttttcttgc ataactggac acagagttgt tattaaagaa agtaag       3150

<210> SEQ ID NO 6
<211> LENGTH: 824
<212> TYPE: PRT
<213> ORGANISM: Unknown
<220> FEATURE:
<223> OTHER INFORMATION: Bacillus sp. KSM-S237

<400> SEQUENCE: 6

Met Met Leu Arg Lys Lys Thr Lys Gln Leu Ile Ser Ser Ile Leu Ile
                -25                 -20                 -15

Leu Val Leu Leu Leu Ser Leu Phe Pro Ala Ala Leu Ala Ala Glu Gly
            -10                  -5                  -1   1

Asn Thr Arg Glu Asp Asn Phe Lys His Leu Leu Gly Asn Asp Asn Val
                 5                  10                  15

Lys Arg Pro Ser Glu Ala Gly Ala Leu Gln Leu Gln Glu Val Asp Gly
 20                  25                  30                  35

Gln Met Thr Leu Val Asp Gln His Gly Glu Lys Ile Gln Leu Arg Gly
                 40                  45                  50

Met Ser Thr His Gly Leu Gln Trp Phe Pro Glu Ile Leu Asn Asp Asn
             55                  60                  65

Ala Tyr Lys Ala Leu Ser Asn Asp Trp Asp Ser Asn Met Ile Arg Leu
```

```
                      70                  75                  80
Ala Met Tyr Val Gly Glu Asn Gly Tyr Ala Thr Asn Pro Glu Leu Ile
                  85                  90                  95

Lys Gln Arg Val Ile Asp Gly Ile Glu Leu Ala Ile Glu Asn Asp Met
100                 105                 110                 115

Tyr Val Ile Val Asp Trp His Val His Ala Pro Gly Asp Pro Arg Asp
                    120                 125                 130

Pro Val Tyr Ala Gly Ala Lys Asp Phe Arg Glu Ile Ala Ala Leu
                135                 140                 145

Tyr Pro Asn Asn Pro His Ile Ile Tyr Glu Leu Ala Asn Glu Pro Ser
                150                 155                 160

Ser Asn Asn Asn Gly Gly Ala Gly Ile Pro Asn Asn Glu Glu Gly Trp
165                 170                 175

Lys Ala Val Lys Glu Tyr Ala Asp Pro Ile Val Glu Met Leu Arg Lys
180                 185                 190                 195

Ser Gly Asn Ala Asp Asp Asn Ile Ile Ile Val Gly Ser Pro Asn Trp
                    200                 205                 210

Ser Gln Arg Pro Asp Leu Ala Ala Asp Asn Pro Ile Asp Asp His His
                215                 220                 225

Thr Met Tyr Thr Val His Phe Tyr Thr Gly Ser His Ala Ala Ser Thr
                230                 235                 240

Glu Ser Tyr Pro Ser Glu Thr Pro Asn Ser Glu Arg Gly Asn Val Met
                245                 250                 255

Ser Asn Thr Arg Tyr Ala Leu Glu Asn Gly Val Ala Val Phe Ala Thr
260                 265                 270                 275

Glu Trp Gly Thr Ser Gln Ala Ser Gly Asp Gly Pro Tyr Phe Asp
                    280                 285                 290

Glu Ala Asp Val Trp Ile Glu Phe Leu Asn Glu Asn Asn Ile Ser Trp
                    295                 300                 305

Ala Asn Trp Ser Leu Thr Asn Lys Asn Glu Val Ser Gly Ala Phe Thr
                310                 315                 320

Pro Phe Glu Leu Gly Lys Ser Asn Ala Thr Asn Leu Asp Pro Gly Pro
325                 330                 335

Asp His Val Trp Ala Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                    360                 365                 370

Tyr Thr Lys Val Leu Trp Asp Phe Asn Asp Gly Thr Lys Gln Gly Phe
                375                 380                 385

Gly Val Asn Ser Asp Ser Pro Asn Lys Glu Leu Ile Ala Val Asp Asn
                390                 395                 400

Glu Asn Asn Thr Leu Lys Val Ser Gly Leu Asp Val Ser Asn Asp Val
                405                 410                 415

Ser Asp Gly Asn Phe Trp Ala Asn Ala Arg Leu Ser Ala Asn Gly Trp
420                 425                 430                 435

Gly Lys Ser Val Asp Ile Leu Gly Ala Glu Lys Leu Thr Met Asp Val
                    440                 445                 450

Ile Val Asp Glu Pro Thr Thr Val Ala Ile Ala Ile Pro Gln Ser
                455                 460                 465

Ser Lys Ser Gly Trp Ala Asn Pro Glu Arg Ala Val Arg Val Asn Ala
        470                 475                 480

Glu Asp Phe Val Gln Gln Thr Asp Gly Lys Tyr Lys Ala Gly Leu Thr
485                 490                 495
```

Ile Thr Gly Glu Asp Ala Pro Asn Leu Lys Asn Ile Ala Phe His Glu
500                 505                 510                 515

Glu Asp Asn Asn Met Asn Ile Ile Leu Phe Val Gly Thr Asp Ala
            520                 525                 530

Ala Asp Val Ile Tyr Leu Asp Asn Ile Lys Val Ile Gly Thr Glu Val
            535                 540                 545

Glu Ile Pro Val Val His Asp Pro Lys Gly Glu Ala Val Leu Pro Ser
            550                 555                 560

Val Phe Glu Asp Gly Thr Arg Gln Gly Trp Asp Trp Ala Gly Glu Ser
565                 570                 575

Gly Val Lys Thr Ala Leu Thr Ile Glu Glu Ala Asn Gly Ser Asn Ala
580                 585                 590                 595

Leu Ser Trp Glu Phe Gly Tyr Pro Glu Val Lys Pro Ser Asp Asn Trp
                600                 605                 610

Ala Thr Ala Pro Arg Leu Asp Phe Trp Lys Ser Asp Leu Val Arg Gly
                615                 620                 625

Glu Asn Asp Tyr Val Ala Phe Asp Phe Tyr Leu Asp Pro Val Arg Ala
                630                 635                 640

Thr Glu Gly Ala Met Asn Ile Asn Leu Val Phe Gln Pro Pro Thr Asn
645                 650                 655

Gly Tyr Trp Val Gln Ala Pro Lys Thr Tyr Thr Ile Asn Phe Asp Glu
660                 665                 670                 675

Leu Glu Glu Ala Asn Gln Val Asn Gly Leu Tyr His Tyr Glu Val Lys
                680                 685                 690

Ile Asn Val Arg Asp Ile Thr Asn Ile Gln Asp Thr Leu Leu Arg
                695                 700                 705

Asn Met Met Ile Ile Phe Ala Asp Val Glu Ser Asp Phe Ala Gly Arg
            710                 715                 720

Val Phe Val Asp Asn Val Arg Phe Glu Gly Ala Thr Thr Glu Pro
            725                 730                 735

Val Glu Pro Glu Pro Val Asp Pro Gly Glu Glu Thr Pro Pro Val Asp
740                 745                 750                 755

Glu Lys Glu Ala Lys Lys Glu Gln Lys Glu Ala Glu Lys Glu Lys
                760                 765                 770

Glu Ala Val Lys Glu Glu Lys Lys Glu Ala Lys Glu Glu Lys Lys Ala
                775                 780                 785

Val Lys Asn Glu Ala Lys Lys Lys
            790                 795

<210> SEQ ID NO 7
<211> LENGTH: 3332
<212> TYPE: DNA
<213> ORGANISM: Unknown
<220> FEATURE:
<223> OTHER INFORMATION: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)

<400> SEQUENCE: 7
agtacttacc attttagagt caaaagatag aagccaagca ggatttgccg atgcaaccgg    60
cttatattta gagggaattt cttttttaaat tgaatacgga ataaaatcag gtaaacaggt   120

```
cctgatttta ttttttttgaa ttttttttgag aactaaagat tgaaatagaa gtagaagaca    180
acggacataa gaaaattgta ttagttttaa ttatagaaaa cgcttttcta taattattta    240
tacctagaac gaaaatactg tttcgaaagc ggtttactat aaaaccttat attccggctc    300 ttttttaaa caggggtga aaattcactc tagtattcta atttcaacat gctataataa      360
atttgtaaga cgcaatatac atctttttt tatgatattt gtaagcggtt aaccttgtgc     420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt ataattttta    600 ggaggtaat atg atg tta aga aag aaa aca aag cag ttg att tct tcc att    651
         Met Met Leu Arg Lys Lys Thr Lys Gln Leu Ile Ser Ser Ile
             -25             -20 ctt att tta gtt tta ctt cta tct tta ttt ccg aca gct ctt gca gca      699
Leu Ile Leu Val Leu Leu Leu Ser Leu Phe Pro Thr Ala Leu Ala Ala
-15              -10                 -5                  -1  1 gaa gga aac act cgt gaa gac aat ttt aaa cat tta tta ggt aat gac      747
Glu Gly Asn Thr Arg Glu Asp Asn Phe Lys His Leu Leu Gly Asn Asp
             5                   10                  15 aat gtt aaa cgc cct tct gag gct ggc gca tta caa tta caa gaa gtc      795
Asn Val Lys Arg Pro Ser Glu Ala Gly Ala Leu Gln Leu Gln Glu Val
             20                  25                  30 gat gga caa atg aca tta gta gat caa cat gga gaa aaa att caa tta      843
Asp Gly Gln Met Thr Leu Val Asp Gln His Gly Glu Lys Ile Gln Leu
         35                  40                  45 cgt gga atg agt aca cac gga tta caa tgg ttt cct gag atc ttg aat      891
Arg Gly Met Ser Thr His Gly Leu Gln Trp Phe Pro Glu Ile Leu Asn
50               55                  60                  65 gat aac gca tac aaa gct ctt gct aac gat tgg gaa tca aat atg att      939
Asp Asn Ala Tyr Lys Ala Leu Ala Asn Asp Trp Glu Ser Asn Met Ile
             70                  75                  80 cgt cta gct atg tat gtc ggt gaa aat ggc tat gct tca aat cca gag      987
Arg Leu Ala Met Tyr Val Gly Glu Asn Gly Tyr Ala Ser Asn Pro Glu
             85                  90                  95 tta att aaa agc aga gtc att aaa gga ata gat ctt gct att gaa aat     1035
Leu Ile Lys Ser Arg Val Ile Lys Gly Ile Asp Leu Ala Ile Glu Asn
             100                 105                 110 gac atg tat gtc atc gtt gat tgg cat gta cat gca cct ggt gat cct     1083
Asp Met Tyr Val Ile Val Asp Trp His Val His Ala Pro Gly Asp Pro
115                 120                 125 aga gat ccc gtt tac gct gga gca gaa gat ttc ttt aga gat att gca     1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag     1179
Ala Leu Tyr Pro Asn Asn Pro His Ile Ile Tyr Glu Leu Ala Asn Glu
             150                 155                 160 cca agt agt aac aat aat ggt gga gct ggg att cca aat aat gaa gaa     1227
Pro Ser Ser Asn Asn Asn Gly Gly Ala Gly Ile Pro Asn Asn Glu Glu
             165                 170                 175 ggt tgg aat gcg gta aaa gaa tac gct gat cca att gta gaa atg tta     1275
Gly Trp Asn Ala Val Lys Glu Tyr Ala Asp Pro Ile Val Glu Met Leu
             180                 185                 190 cgt gat agc ggg aac gca gat gac aat att atc att gtg ggt agt cca     1323
Arg Asp Ser Gly Asn Ala Asp Asp Asn Ile Ile Ile Val Gly Ser Pro
195                 200                 205 aac tgg agt cag cgt cct gac tta gca gct gat aat cca att gat gat     1371
Asn Trp Ser Gln Arg Pro Asp Leu Ala Ala Asp Asn Pro Ile Asp Asp
210                 215                 220                 225
```

```
cac cat aca atg tat act gtt cac ttc tac act ggt tca cat gct gct      1419
His His Thr Met Tyr Thr Val His Phe Tyr Thr Gly Ser His Ala Ala
            230             235             240 tca act gaa agc tat ccg cct gaa act cct aac tct gaa aga gga aac      1467
Ser Thr Glu Ser Tyr Pro Pro Glu Thr Pro Asn Ser Glu Arg Gly Asn
            245             250             255 gta atg agt aac act cgt tat gcg tta gaa aac gga gta gca gta ttt      1515
Val Met Ser Asn Thr Arg Tyr Ala Leu Glu Asn Gly Val Ala Val Phe
            260             265             270 gca aca gag tgg gga act agc caa gca aat gga gat ggt ggt cct tac      1563
Ala Thr Glu Trp Gly Thr Ser Gln Ala Asn Gly Asp Gly Gly Pro Tyr
        275             280             285 ttt gat gaa gca gat gta tgg att gag ttt tta aat gaa aac aac att      1611
Phe Asp Glu Ala Asp Val Trp Ile Glu Phe Leu Asn Glu Asn Asn Ile
290             295             300             305 agc tgg gct aac tgg tct tta acg aat aaa aat gaa gta tct ggt gca      1659
Ser Trp Ala Asn Trp Ser Leu Thr Asn Lys Asn Glu Val Ser Gly Ala
            310             315             320 ttt aca cca ttc gag tta ggt aag tct aac gca aca agt ctt gac cca      1707
Phe Thr Pro Phe Glu Leu Gly Lys Ser Asn Ala Thr Ser Leu Asp Pro
        325             330             335 ggg cca gac caa gta tgg gta cca gaa gag tta agt ctt tct gga gaa      1755
Gly Pro Asp Gln Val Trp Val Pro Glu Glu Leu Ser Leu Ser Gly Glu
        340             345             350 tat gta cgt gct cgt att aaa ggt gtg aac tat gag cca atc gac cgt      1803
Tyr Val Arg Ala Arg Ile Lys Gly Val Asn Tyr Glu Pro Ile Asp Arg
            355             360             365 aca aaa tac acg aaa gta ctt tgg gac ttt aat gat gga acg aag caa      1851
Thr Lys Tyr Thr Lys Val Leu Trp Asp Phe Asn Asp Gly Thr Lys Gln
370             375             380             385 gga ttt gga gtg aat gga gat tct cca gtt gaa gat gta gtt att gag      1899
Gly Phe Gly Val Asn Gly Asp Ser Pro Val Glu Asp Val Val Ile Glu
            390             395             400 aat gaa gcg ggc gct tta aaa ctt tca gga tta gat gca agt aat gat      1947
Asn Glu Ala Gly Ala Leu Lys Leu Ser Gly Leu Asp Ala Ser Asn Asp
        405             410             415 gtt tct gaa ggt aat tac tgg gct aat gct cgt ctt tct gcc gac ggt      1995
Val Ser Glu Gly Asn Tyr Trp Ala Asn Ala Arg Leu Ser Ala Asp Gly
        420             425             430 tgg gga aaa agt gtt gat att tta ggt gct gaa aaa ctt act atg gat      2043
Trp Gly Lys Ser Val Asp Ile Leu Gly Ala Glu Lys Leu Thr Met Asp
            435             440             445 gtg att gtt gat gag ccg acc acg gta tca att gct gca att cca caa      2091
Val Ile Val Asp Glu Pro Thr Thr Val Ser Ile Ala Ala Ile Pro Gln
450             455             460             465 ggg cca tca gcc aat tgg gtt aat cca aat cgt gca att aag gtt gag      2139
Gly Pro Ser Ala Asn Trp Val Asn Pro Asn Arg Ala Ile Lys Val Glu
            470             475             480 cca act aat ttc gta ccg tta gga gat aag ttt aaa gcg gaa tta act      2187
Pro Thr Asn Phe Val Pro Leu Gly Asp Lys Phe Lys Ala Glu Leu Thr
            485             490             495 ata act tca gct gac tct cca tcg tta gaa gct att gcg atg cat gct      2235
Ile Thr Ser Ala Asp Ser Pro Ser Leu Glu Ala Ile Ala Met His Ala
            500             505             510 gaa aat aac aac atc aac aac atc att ctt ttt gta gga act gaa ggt      2283
Glu Asn Asn Asn Ile Asn Asn Ile Ile Leu Phe Val Gly Thr Glu Gly
        515             520             525 gct gat gtt atc tat tta gat aac att aaa gta att gga aca gaa gtt      2331
Ala Asp Val Ile Tyr Leu Asp Asn Ile Lys Val Ile Gly Thr Glu Val
530             535             540             545
```

```
gaa att cca gtt gtt cat gat cca aaa gga gaa gct gtt ctt cct tct    2379
Glu Ile Pro Val Val His Asp Pro Lys Gly Glu Ala Val Leu Pro Ser
            550                 555                 560 gtt ttt gaa gac ggt aca cgt caa ggt tgg gac tgg gct gga gag tct    2427
Val Phe Glu Asp Gly Thr Arg Gln Gly Trp Asp Trp Ala Gly Glu Ser
565                 570                 575 ggt gtg aaa aca gct tta aca att gaa gaa gca aac ggt tct aac gcg    2475
Gly Val Lys Thr Ala Leu Thr Ile Glu Glu Ala Asn Gly Ser Asn Ala
        580                 585                 590 tta tca tgg gaa ttt gga tac cca gaa gta aaa cct agt gat aac tgg    2523
Leu Ser Trp Glu Phe Gly Tyr Pro Glu Val Lys Pro Ser Asp Asn Trp
    595                 600                 605 gca aca gct cca cgt tta gat ttc tgg aaa tct gac ttg gtt cgc ggt    2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca    2619
Glu Asn Asp Tyr Val Thr Phe Asp Phe Tyr Leu Asp Pro Val Arg Ala
                630                 635                 640 aca gaa ggc gca atg aat atc aat tta gta ttc cag cca cct act aac    2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa    2715
Gly Tyr Trp Val Gln Ala Pro Lys Thr Tyr Thr Ile Asn Phe Asp Glu
        660                 665                 670 tta gag gaa gcg aat caa gta aat ggt tta tat cac tat gaa gtg aaa    2763
Leu Glu Glu Ala Asn Gln Val Asn Gly Leu Tyr His Tyr Glu Val Lys
    675                 680                 685 att aac gta aga gat att aca aac att caa gat gac acg tta cta cgt    2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga    2859
Asn Met Met Ile Ile Phe Ala Asp Val Glu Ser Asp Phe Ala Gly Arg
                710                 715                 720 gtc ttt gta gat aat gtt cgt ttt gag ggg gct gct act act gag ccg    2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat    2955
Val Glu Pro Glu Pro Val Asp Pro Gly Glu Glu Thr Pro Pro Val Asp
        740                 745                 750 gag aag gaa gcg aaa aaa gaa caa aaa gaa gca gag aaa gaa gag aaa    3003
Glu Lys Glu Ala Lys Lys Glu Gln Lys Glu Ala Glu Lys Glu Glu Lys
    755                 760                 765 gaa gca gta aaa gaa gaa aag aaa gaa gct aaa gaa gaa aag aaa gca    3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct   3105
Ile Lys Asn Glu Ala Thr Lys Lys
                790 aaaggtctga tgcagatctt ttagataacc ttttttgca taactggaca tagaatggtt    3165 attaaagaaa gcaaggtgtt tatacgatat taaaaggta gcgattttaa attgaaacct    3225 ttaataatgt cttgtgatag aatgatgaag taatttaaga gggggaaacg aagtgaaaac    3285 ggaaatttct agtagaagaa aaacagacca agaaatactg caagctt    3332

<210> SEQ ID NO 8
<211> LENGTH: 822
<212> TYPE: PRT
<213> ORGANISM: Unknown
<220> FEATURE:
<223> OTHER INFORMATION: Bacillus sp. KSM-64
```

```
<400> SEQUENCE: 8

Met Met Leu Arg Lys Lys Thr Lys Gln Leu Ile Ser Ser Ile Leu Ile
            -25                 -20                 -15

Leu Val Leu Leu Leu Ser Leu Phe Pro Thr Ala Leu Ala Ala Glu Gly
            -10                  -5              -1   1

Asn Thr Arg Glu Asp Asn Phe Lys His Leu Leu Gly Asn Asp Asn Val
          5                  10                 15

Lys Arg Pro Ser Glu Ala Gly Ala Leu Gln Leu Gln Glu Val Asp Gly
 20              25                  30                      35

Gln Met Thr Leu Val Asp Gln His Gly Glu Lys Ile Gln Leu Arg Gly
                 40                  45                 50

Met Ser Thr His Gly Leu Gln Trp Phe Pro Glu Ile Leu Asn Asp Asn
                 55                  60                 65

Ala Tyr Lys Ala Leu Ala Asn Asp Trp Glu Ser Asn Met Ile Arg Leu
             70                  75              80

Ala Met Tyr Val Gly Glu Asn Gly Tyr Ala Ser Asn Pro Glu Leu Ile
             85                  90              95

Lys Ser Arg Val Ile Lys Gly Ile Asp Leu Ala Ile Glu Asn Asp Met
100             105                 110                     115

Tyr Val Ile Val Asp Trp His Val His Ala Pro Gly Asp Pro Arg Asp
                120                 125                 130

Pro Val Tyr Ala Gly Ala Glu Asp Phe Phe Arg Asp Ile Ala Ala Leu
            135                 140                 145

Tyr Pro Asn Asn Pro His Ile Ile Tyr Glu Leu Ala Asn Glu Pro Ser
            150                 155                 160

Ser Asn Asn Asn Gly Gly Ala Gly Ile Pro Asn Asn Glu Glu Gly Trp
165                 170                 175

Asn Ala Val Lys Glu Tyr Ala Asp Pro Ile Val Glu Met Leu Arg Asp
180             185                 190                     195

Ser Gly Asn Ala Asp Asn Ile Ile Ile Val Gly Ser Pro Asn Trp
                200                 205                 210

Ser Gln Arg Pro Asp Leu Ala Ala Asp Asn Pro Ile Asp Asp His His
            215                 220                 225

Thr Met Tyr Thr Val His Phe Tyr Thr Gly Ser His Ala Ala Ser Thr
            230                 235                 240

Glu Ser Tyr Pro Pro Glu Thr Pro Asn Ser Glu Arg Gly Asn Val Met
            245                 250                 255

Ser Asn Thr Arg Tyr Ala Leu Glu Asn Gly Val Ala Val Phe Ala Thr
260             265                 270                     275

Glu Trp Gly Thr Ser Gln Ala Asn Gly Asp Gly Gly Pro Tyr Phe Asp
                280                 285                 290

Glu Ala Asp Val Trp Ile Glu Phe Leu Asn Glu Asn Asn Ile Ser Trp
            295                 300                 305

Ala Asn Trp Ser Leu Thr Asn Lys Asn Glu Val Ser Gly Ala Phe Thr
            310                 315                 320

Pro Phe Glu Leu Gly Lys Ser Asn Ala Thr Ser Leu Asp Pro Gly Pro
325                 330                 335

Asp Gln Val Trp Val Pro Glu Glu Leu Ser Leu Ser Gly Glu Tyr Val
340             345                 350                     355

Arg Ala Arg Ile Lys Gly Val Asn Tyr Glu Pro Ile Asp Arg Thr Lys
                360                 365                 370

Tyr Thr Lys Val Leu Trp Asp Phe Asn Asp Gly Thr Lys Gln Gly Phe
            375                 380                 385
```

```
Gly Val Asn Gly Asp Ser Pro Val Glu Asp Val Val Ile Glu Asn Glu
            390                 395                 400

Ala Gly Ala Leu Lys Leu Ser Gly Leu Asp Ala Ser Asn Asp Val Ser
405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
                440                 445                 450

Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
        470                 475                 480

Asn Phe Val Pro Leu Gly Asp Lys Phe Lys Ala Glu Leu Thr Ile Thr
485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
                520                 525                 530

Val Ile Tyr Leu Asp Asn Ile Lys Val Ile Gly Thr Glu Val Glu Ile
            535                 540                 545

Pro Val Val His Asp Pro Lys Gly Glu Ala Val Leu Pro Ser Val Phe
        550                 555                 560

Glu Asp Gly Thr Arg Gln Gly Trp Asp Trp Ala Gly Glu Ser Gly Val
565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
                600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
        630                 635                 640

Gly Ala Met Asn Ile Asn Leu Val Phe Gln Pro Thr Asn Gly Tyr
645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
                680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
        710                 715                 720

Val Asp Asn Val Arg Phe Glu Gly Ala Ala Thr Thr Glu Pro Val Glu
725                 730                 735

Pro Glu Pro Val Asp Pro Gly Glu Glu Thr Pro Pro Val Asp Glu Lys
740                 745                 750                 755

Glu Ala Lys Lys Glu Gln Lys Glu Ala Lys Glu Glu Lys Glu Ala
                760                 765                 770

Val Lys Glu Glu Lys Lys Glu Ala Lys Glu Lys Lys Ala Ile Lys
            775                 780                 785

Asn Glu Ala Thr Lys Lys
            790
```

<210> SEQ ID NO 9

```
<211> LENGTH: 230
<212> TYPE: DNA
<213> ORGANISM: Bacillus subtilis

<400> SEQUENCE: 9
gttagtcgag atcgaagtta ttgcactggt gaaataataa gaaaagtgat tctgggagag      60
ccgggatcac ttttttattt accttatgcc cgaaatgaaa gctttatgac ctaattgtgt     120
aactatatcc tattttttca aaaatatttt aaaaacgag caggatttca gaaaaaatcg     180
tggaattgat acactaatgc ttttatatag ggaaaaggtg gtgaactact                230

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 10
gttagtcgag atcgaagtta                                                  20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 11
agtagttcac cacctttcc                                                   20

<210> SEQ ID NO 12
<211> LENGTH: 40
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of Bacillus subtilis gene,
      prsA and a 5'-portion designed from the nucleotide sequence of
      5'-flanking region of Bacillus subtilis gene, spoVG

<400> SEQUENCE: 12
ggaaaaggtg gtgaactact atgaagaaaa tcgcaatagc                            40

<210> SEQ ID NO 13
<211> LENGTH: 40
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of Bacillus subtilis gene,
      prsA and a 5'-portion designed from the nucleotide sequence of
      plasmid pMUTIN4

<400> SEQUENCE: 13
tttgcactga ttggtgtatc ttatttagaa ttgcttgaag                            40

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide as the forward PCR primer used
      for the amplification of erythromycin resistant gene from plasmid
``` pMUTIN4

<400> SEQUENCE: 14
gatacaccaa tcagtgcaaa                                                20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide as the reverse PCR primer used
      for the amplification of erythromycin resistant gene from plasmid
      pMUTIN4

<400> SEQUENCE: 15
caagagtttg tagaaacgca                                                20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 16
taagaaaagt gattctggga                                                20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of Bacillus subtilis gene, amyE

<400> SEQUENCE: 17
ggagtgtcaa gaatgtttgc                                                20

<210> SEQ ID NO 18
<211> LENGTH: 40
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      5'-flanking region of Bacillus subtilis gene, spoVG

<400> SEQUENCE: 18
tcccagaatc acttttctta atcatcgctc atccatgtcg                          40

<210> SEQ ID NO 19
<211> LENGTH: 40
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      plasmid pMUTIN4

<400> SEQUENCE: 19
tgcgtttcta caaactcttg gtttaggctg ggcggtgata                          40

<210> SEQ ID NO 20
<211> LENGTH: 18

```
<212> TYPE: DNA
<213> ORGANISM: Artificial Sequence
<220> FEATURE:
<223> OTHER INFORMATION: Oligonucleotide as PCR primer designed from the
      nucleotide sequence of Bacillus subtilis gene, amyE

<400> SEQUENCE: 20
tcaatgggga agagaacc                                                      18

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of Bacillus subtilis gene, amyE

<400> SEQUENCE: 21
tcaaaacctc tttactgccg                                                    20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of Bacillus subtilis gene, amyE

<400> SEQUENCE: 22
cacgtaatca aagccaggct                                                    20

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide as PCR primer designed from the
      nucleotide sequence of the upstream region of the alkaline
      cellulase gene in Bacillus sp. KSM-S237 with a insertion of the
      BamHI restriction site at the 5'-end

<400> SEQUENCE: 23
cccggatcca acaggcttat attta                                              25

<210> SEQ ID NO 24
<211> LENGTH: 29
<212> TYPE: DNA
<213> ORGANISM: Artificial Sequence
<220> FEATURE:
<223> OTHER INFORMATION: Oligonucleotide as PCR primer; its 3'-portion
      designed from nucleotide sequence of the alkaline cellulase gene
      in Bacillus sp. KSM-S237 and its 5'-portion designed from
      nucleotide sequence of the alkaline amylase gene in Bacillus sp.
      KSM-K38

<400> SEQUENCE: 24
ttcaatccat ctgctgcaag agctgccgg                                          29

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide as PCR primer; its 3'-portion
      designed from nucleotide sequence of the alkaline amylase gene in
      Bacillus sp. KSM-K38 and its 5'-portion designed from nucleotide
      sequence of the alkaline cellulase gene in Bacillus sp. KSM-S237

<400> SEQUENCE: 25
```

```
gctcttgcag cagatggatt gaacggtacg                                    30
```

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide as PCR primer designed from
      nucleotide sequence of the downstream region of the alkaline
      amylase gene in Bacillus sp. KSM-K38 with a insertion of the XbaI
      restriction site at the 5'-end

<400> SEQUENCE: 26

```
ttggtctaga ccccaagctt caaagtcgta                                    30
```

<210> SEQ ID NO 27
<211> LENGTH: 19
<212> TYPE: DNA
<213> ORGANISM: Artificial Sequence
<220> FEATURE:
<223> OTHER INFORMATION: Oligonucleotide as the forward PCR primer used
      for the amplification of chloramphenicol resistant gene from
      plasmid pC194

<400> SEQUENCE: 27

```
caactaaagc acccattag                                                19
```

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide as the forward PCR primer used
      for the amplification of chloramphenicol resistant gene from
      plasmid pC194

<400> SEQUENCE: 28

```
cttcaactaa cggggcag                                                 18
```

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, abrB

<400> SEQUENCE: 29

```
ttgatcaatt caactgggtg                                               20
```

<210> SEQ ID NO 30
<211> LENGTH: 39
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 5'-flanking region of
      Bacillus subtilis gene, abrB and a 5'-portion designed from the
      nucleotide sequence of plasmid pC194

<400> SEQUENCE: 30

```
ctaatgggtg ctttagttgt ctcctcccaa gagatactt                          39
```

<210> SEQ ID NO 31
<211> LENGTH: 40
<212> TYPE: DNA
<213> ORGANISM: Artificial Sequence
<220> FEATURE:

-continued

<223> OTHER INFORMATION: Oligonucleotide as PCR primer with a 3'-portion
designed from the nucleotide sequence of 3'-flanking region of
Bacillus subtilis gene, abrB and a 5'-portion designed from the
nucleotide sequence of plasmid pC194

<400> SEQUENCE: 31
ctgccccgtt agttgaagaa tcatttcttg tacaaaaaac                40

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide as PCR primer designed from the
nucleotide sequence of 3'-flanking region of Bacillus subtilis
gene, abrB

<400> SEQUENCE: 32
tttcaaaaaa ctaactcgga a                                   21

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide as PCR primer designed from the
nucleotide sequence of 5'-flanking region of Bacillus subtilis
gene, abrB

<400> SEQUENCE: 33
caatatcaac gagctgagtt                                     20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide as PCR primer designed from the
nucleotide sequence of 3'-flanking region of Bacillus subtilis
gene, abrB

<400> SEQUENCE: 34
atgttaaggc gccaaatgag                                     20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide as PCR primer designed from the
nucleotide sequence of 5'-flanking region of Bacillus subtilis
gene, dltB

<400> SEQUENCE: 35
taaaccaagc gccgttctca                                     20

<210> SEQ ID NO 36
<211> LENGTH: 39
<212> TYPE: DNA
<213> ORGANISM: Artificial Sequence
<220> FEATURE:
<223> OTHER INFORMATION: Oligonucleotide as PCR primer with a 3'-portion
designed from the nucleotide sequence of 5'-flanking region of
Bacillus subtilis gene, dltB and a 5'-portion designed from the
nucleotide sequence of plasmid pC194

<400> SEQUENCE: 36
ctaatgggtg ctttagttgc agaagaagaa tgccaagca                39

```
<210> SEQ ID NO 37
<211> LENGTH: 38
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 3'-flanking region of
      Bacillus subtilis gene, dltB and a 5'-portion designed from the
      nucleotide sequence of plasmid pC194

<400> SEQUENCE: 37
ctgccccgtt agttgaagtt tctcaggaaa accatttc                              38

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltB

<400> SEQUENCE: 38
cttatccttt actgactgcg                                                  20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, dltB

<400> SEQUENCE: 39
tttacattgc gtgacaaagg                                                  20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltB

<400> SEQUENCE: 40
ttcttttcca gcatgctgta                                                  20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, dltD

<400> SEQUENCE: 41
cgacagatac cgccggttcg                                                  20

<210> SEQ ID NO 42
<211> LENGTH: 39
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 5'-flanking region of
      Bacillus subtilis gene, dltD and a 5'-portion designed from the
```

-continued nucleotide sequence of plasmid pC194

<400> SEQUENCE: 42
ctaatgggtg ctttagttgt gcgaatagaa taaacgcca                                   39

<210> SEQ ID NO 43
<211> LENGTH: 38
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 3'-flanking region of
      Bacillus subtilis gene, dltD and a 5'-portion designed from the
      nucleotide sequence of plasmid pC194

<400> SEQUENCE: 43
ctgccccgtt agttgaaggc atctcatagg acgcggct                                    38

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltD

<400> SEQUENCE: 44
tgtttagtca tggtcaatct                                                        20

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, dltD

<400> SEQUENCE: 45
tatacgggaa tccataaaat c                                                      21

<210> SEQ ID NO 46
<211> LENGTH: 21
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltD

<400> SEQUENCE: 46
ttctattgta taccttcaac a                                                      21

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, dltA

<400> SEQUENCE: 47
ccagctgctg ctggcacaaa                                                        20

<210> SEQ ID NO 48
<211> LENGTH: 40

```
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 5'-flanking region of
      Bacillus subtilis gene, dltA and a 5'-portion designed from the
      nucleotide sequence of plasmid pC194

<400> SEQUENCE: 48
ctaatgggtg ctttagttga gttattctct ctccaattag                           40

<210> SEQ ID NO 49
<211> LENGTH: 39
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of 3'-flanking region of
      Bacillus subtilis gene, dltE and a 5'-portion designed from the
      nucleotide sequence of plasmid pC194

<400> SEQUENCE: 49
ctgccccgtt agttgaagtt tctcctgctt ttttcatat                            39

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltE

<400> SEQUENCE: 50
atgacctcat cgatcgcaat                                                 20

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide as PCR primer designed from the
      nucleotide sequence of 5'-flanking region of Bacillus subtilis
      gene, dltA

<400> SEQUENCE: 51
aaaatcgttt taggcttcat t                                               21

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide as PCR primer designed from the
      nucleotide sequence of 3'-flanking region of Bacillus subtilis
      gene, dltE

<400> SEQUENCE: 52
aattgcgcgt aatgccttcc                                                 20

<210> SEQ ID NO 53
<211> LENGTH: 42
<212> TYPE: DNA
<213> ORGANISM: Artificial Sequence
<220> FEATURE:
<223> OTHER INFORMATION: Oligonucleotide as PCR primer with a 3'-portion
      designed from the nucleotide sequence of Bacillus cereus gene,
      prsA and a 5'-portion designed from the nucleotide sequence of
      5'-flanking region of Bacillus subtilis gene, spoVG
```

<400> SEQUENCE: 53
ggaaaaggtg gtgaactact atgaagaaag ctatgcttgc ct          42

<210> SEQ ID NO 54
<211> LENGTH: 45
<212> TYPE: DNA
<213> ORGANISM: Artificial Sequence
<220> FEATURE:
<223> OTHER INFORMATION: Oligonucleotide as PCR primer with a 3'-portion
   designed from the nucleotide sequence of Bacillus cereus gene,
   prsA and a 5'-portion designed from the nucleotide sequence of
   plasmid pMUTIN4

<400> SEQUENCE: 54
gcactgattg gtgtatctta tttcttttct tcttttttat cgtca       45

<210> SEQ ID NO 55
<211> LENGTH: 861
<212> TYPE: DNA
<213> ORGANISM: Bacillus cereus
<220> FEATURE:
<221> NAME/KEY: CDS
<222> LOCATION: (1)..(861)

<400> SEQUENCE: 55

| atg | aag | aaa | gct

```
gga gac ctt ggc tac ttt act gct ggt aaa atg gtt aaa gaa ttc gaa       576
Gly Asp Leu Gly Tyr Phe Thr Ala Gly Lys Met Val Lys Glu Phe Glu
            180                 185                 190 gat gct gct tac aag ctg aaa aaa gat gaa gta agc gaa cct gtg aaa       624
Asp Ala Ala Tyr Lys Leu Lys Lys Asp Glu Val Ser Glu Pro Val Lys
        195                 200                 205 tca caa ttc ggt tac cac atc att aaa gta aca gac att aaa gaa caa       672
Ser Gln Phe Gly Tyr His Ile Ile Lys Val Thr Asp Ile Lys Glu Gln
    210                 215                 220 aaa cca ttt gat gaa gta aaa ggc gac atc aaa aaa gat cta gtt cag       720
Lys Pro Phe Asp Glu Val Lys Gly Asp Ile Lys Lys Asp Leu Val Gln
225                 230                 235                 240 aaa aaa gca caa gat gct gca ttc atg aat gat ctt atg atg aaa gaa       768
Lys Lys Ala Gln Asp Ala Ala Phe Met Asn Asp Leu Met Met Lys Glu
                245                 250                 255 atc aaa aaa gct gac gta aaa gtt gac gat aaa gat tta aaa gat ctt       816
Ile Lys Lys Ala Asp Val Lys Val Asp Asp Lys Asp Leu Lys Asp Leu
            260                 265                 270 ttc gaa gag aaa aaa gct gac gat aaa aaa gaa gaa aag aaa taa           861
Phe Glu Glu Lys Lys Ala Asp Asp Lys Lys Glu Glu Lys Lys
        275                 280                 285
```

<210> SEQ ID NO 56
<211> LENGTH: 286
<212> TYPE: PRT
<213> ORGANISM: Bacillus cereus

<400> SEQUENCE: 56

Met Lys Lys Ala Met Leu Ala Leu Ala Ala Thr Ser Val Ile Ala Leu
1               5                   10                  15

Ser Ala Cys Gly Thr Ser Ser Asp Lys Ile Val Thr Ser Lys Ala
            20                  25                  30

Gly Asp Ile Thr Lys Glu Glu Phe Tyr Asp Gln Met Lys Thr Gln Ala
        35                  40                  45

Gly Lys Gln Val Leu Asn Asn Met Val Met Glu Lys Val Leu Ile Lys
    50                  55                  60

Asn Tyr Lys Val Glu Asp Lys Val Asp Lys Lys Phe Asp Glu Met
65                  70                  75                  80

Lys Lys Gln Tyr Gly Asp Gln Phe Asp Thr Leu Leu Lys Gln Gly
                85                  90                  95

Ile Lys Glu Glu Thr Ile Lys Thr Gly Val Arg Ala Gln Leu Ala Gln
            100                 105                 110

Glu Lys Ala Ile Glu Lys Thr Ile Thr Asp Lys Glu Leu Lys Glu Asn
        115                 120                 125

Tyr Lys Pro Glu Ile Lys Ala Ser His Ile Leu Val Lys Asp Glu Ala
    130                 135                 140

Thr Ala Lys Lys Val Lys Glu Glu Leu Gly Gln Gly Lys Ser Phe Glu
145                 150                 155                 160

Glu Leu Ala Lys Gln Tyr Ser Glu Asp Thr Gly Ser Lys Glu Lys Gly
                165                 170                 175

Gly Asp Leu Gly Tyr Phe Thr Ala Gly Lys Met Val Lys Glu Phe Glu
            180                 185                 190

Asp Ala Ala Tyr Lys Leu Lys Lys Asp Glu Val Ser Glu Pro Val Lys
        195                 200                 205

Ser Gln Phe Gly Tyr His Ile Ile Lys Val Thr Asp Ile Lys Glu Gln
    210                 215                 220

Lys Pro Phe Asp Glu Val Lys Gly Asp Ile Lys Lys Asp Leu Val Gln
225                 230                 235                 240

```
Lys Lys Ala Gln Asp Ala Ala Phe Met Asn Asp Leu Met Met Lys Glu
            245                 250                 255

Ile Lys Lys Ala Asp Val Lys Val Asp Asp Lys Asp Leu Lys Asp Leu
            260                 265                 270

Phe Glu Glu Lys Lys Ala Asp Asp Lys Lys Glu Glu Lys Lys
        275                 280                 285
```

RECOMBINANT MICROORGANISM

REFERENCE TO SEQUENCE LISTING SUBMITTED ELECTRONICALLY

The content of the electronically submitted substitute sequence listing, file name: 2537_0250000_Seq_List_ascii.txt; Size 83,271 bytes; and Date of Creation: Jun. 2, 2010, filed herewith, is incorporated herein by reference in its entirety.

FIELD OF THE INVENTION

The present invention relates to a recombinant microorganism employed for the production of a useful protein or polypeptide, and to a method for producing the protein or polypeptide.

BACKGROUND OF THE INVENTION

Microorganisms are widely used for industrially producing a broad range of useful substances, including alcoholic beverages, certain types of foods such as bean paste (miso) and soy sauce (shoyu), amino acids, organic acids, nucleic-acid-related substances, antibiotics, carbohydrates, lipids, and proteins. Also, these substances are used in a variety of fields, including foods, pharmaceuticals, detergents, products for daily use such as cosmetics, and various chemical raw materials.

In industrial production of useful substances by means of microorganisms, improvement of productivity is one major topic of interest, and one approach therefor is breeding of microorganisms through mutagenesis or other genetic techniques. Recently, in particular, with advancement of microbial genetics and biotechnology, more effective breeding of useful microorganisms has been performed through genetic recombination or other techniques.

In addition, in association with recent rapid development of genome analysis techniques, attempts have been made to actively apply the genomic information of microorganisms of interest to industrial uses. Industrially useful host microorganisms whose genomic information has been disclosed include *Bacillus subtilis* Marburg No. 168 (Non-Patent Document 1), *Escherichia coli* K-12 MG1655 (Non-Patent Document 2), and *Corynebacterium glutamicum* ATCC132032. Such microorganisms have been improved on the basis of the disclosed genomic information.

However, despite the aforementioned attempts, their efficiency of producing useful substances has not necessarily been satisfactory.

A prsA gene has been found as a gene involved in a protein secretion process in *Bacillus subtilis*, and hitherto conducted studies have suggested that PrsA has a chaperone-like function of facilitating folding of the protein transported to the outside of the cytoplasm through the cell membrane. Meanwhile, there has been reported a microorganism in which productivity of a protein of interest is improved by introducing therein a plasmid in which a *Bacillus subtilis* prsA gene including the promoter region of the gene has been inserted, so that the microorganism has a plurality of prsA genes (Non-Patent Document 3).

However, this microorganism poses practical difficulties because the number of plasmids introduced into one cell is difficult to be controlled, and removal of plasmids often occurs during culturing the microorganism.

As has also been reported, a cloning vector pHP13 in which a prsA gene fragment has been inserted exhibits a function of replicating a *Bacillus subtilis* plasmid pTA1060 (Non-Patent Document 4), and the average number of pTA1060 copies for one *Bacillus subtilis* genome, i.e. one *Bacillus subtilis* cell, is 5.2 (Non-Patent Document 5).

Since the amount of a protein of interest produced by the above-reported microorganism is 1 to 5 times that produced by a wild-type strain, the amount of a protein of interest produced per introduced prsA gene is about 0.2 to about 1 times that produced by the wild-type strain. Therefore, satisfactory effects are not obtained through introduction of the prsA gene.

As has been reported, in *Bacillus subtilis*, the abrB gene encodes a transcription factor which plays an important role in controlling expression of various genes involved in, for example, sporulation, competence, or nutrition acquisition during the transition from logarithmic growth phase to stationary phase (Non-Patent Documents 6 and 7).

As has been known, dltA, dltB, dltC, dltD, and dltE genes belong to the same operon, and these genes are involved in addition of D-alanine to teichoic acid present in the cell wall and the cell membrane. As has also been reported, protein secretion is improved through inhibition of the functions of these genes (Non-Patent Documents 8 to 10).

However, there has not yet been known a microorganism which overexpresses a prsA gene, and in which an abrB gene, a dltA gene, a dltB gene, a dltC gene, a dltD gene, or a dltE gene is inactivated. In addition, such a microorganism is not even expected to exhibit excellent productivity of a useful protein or polypeptide as compared with a microorganism which overexpresses a prsA gene.

Non-Patent Document 1: Nature, 390, 249, 1997
Non-Patent Document 2: Science, 277, 1453, 1997
Non-Patent Document 3: Mol. Microbiol., 8: 727 (1993)
Non-Patent Document 4: Mol. Gen. Genet., 209: 335 (1987)
Non-Patent Document 5: Plasmid, 18: 8 (1987)
Non-Patent Document 6: Mol. Microbiol., 7: 337 (1993)
Non-Patent Document 7: Cell Mol. Life. Sci., 59: 392 (2002)
Non-Patent Document 8: J. Biol. Chem., 270: 15598 (1995)
Non-Patent Document 9: Microbiology, 145: 3409 (1999)
Non-Patent Document 10: Appl. Environ. Microbiol., 68: 227 (2002)

SUMMARY OF THE INVENTION

The present invention provides the following.

(1) A recombinant microorganism produced by transferring a gene encoding a protein or polypeptide of interest to a microorganism strain, wherein the microorganism strain is prepared by:

introducing a transcription initiation regulatory region that functions in the microorganism or both the transcription initiation regulatory region and a ribosome-binding site that functions in the microorganism into the upstream of a *Bacillus subtilis* prsA gene or a gene corresponding thereto in the genome of a parental microorganism, or by introducing a gene fragment prepared by ligating a transcription initiation regulatory region that functions in the microorganism or both the transcription initiation regulatory region and a ribosome-binding site that functions in the microorganism to the upstream of the *Bacillus subtilis* prsA gene or a gene corresponding thereto into the genome of a parental microorganism; and deleting or inactivating one or more genes selected from an abrB gene, a dltA gene, a dltB gene, a dltC gene, a dltD gene, a dltE gene and a gene corresponding thereto.

(2) A method for producing a protein or polypeptide of interest, including employing the recombinant microorganism.

DETAILED DESCRIPTION OF THE INVENTION

Figure 1:
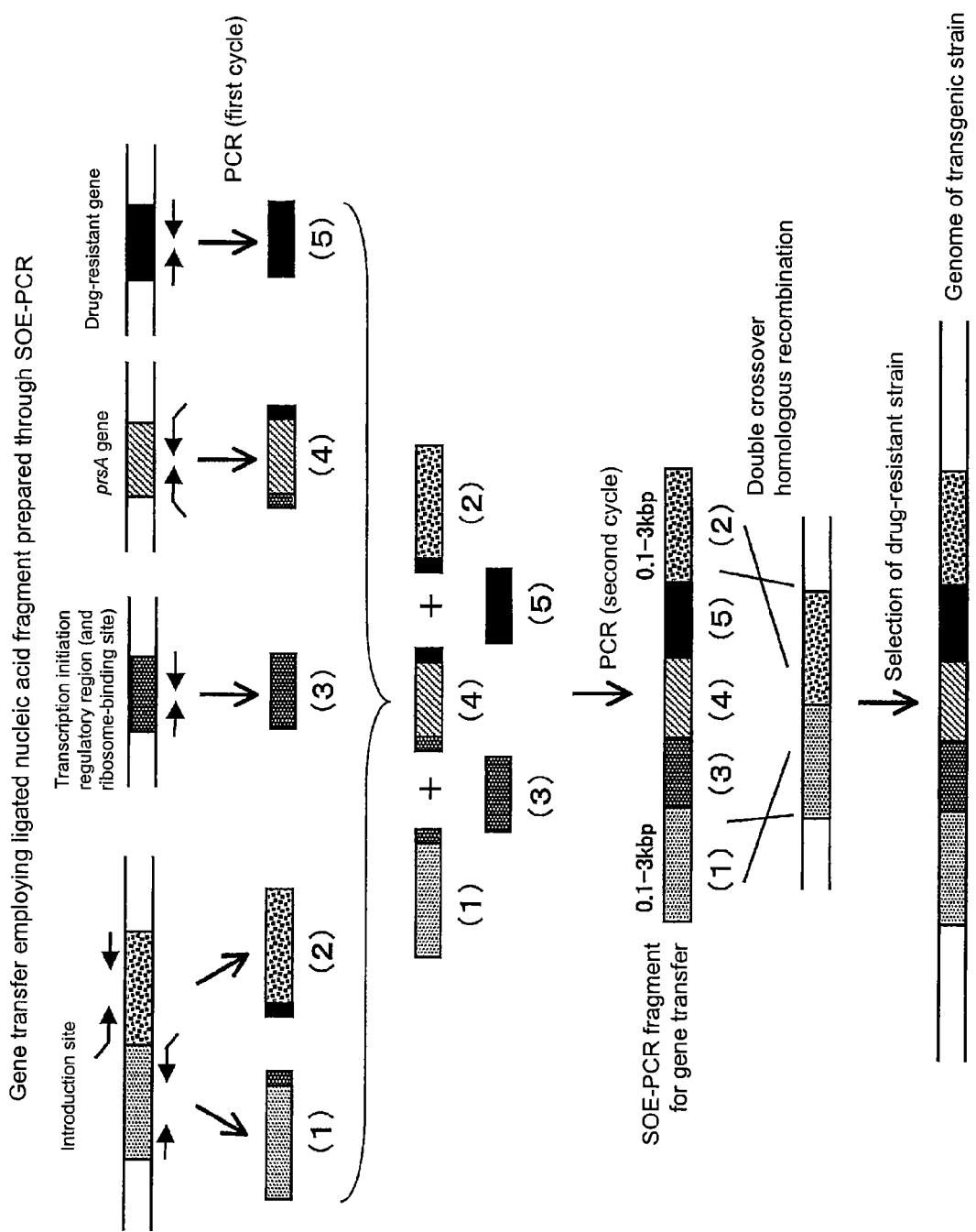
FIG. 1 schematically shows gene transfer employing a ligated nucleic acid fragment prepared through SOE-PCR.

The present invention is directed to provision of a microorganism having improved productivity of a protein or polypeptide of interest, and to a method for producing a protein or polypeptide of interest by use of the microorganism.

The present inventors have studied various genes encoded on the genomes of microorganisms to search genes which affect the production of useful proteins or polypeptides, and have found that when a gene encoding a protein or polypeptide of interest is introduced into a microorganism strain which has been modified so as to enhance expression of a *Bacillus subtilis* prsA gene for overexpression of *Bacillus subtilis* PrsA, and to suppress expression of an abrB gene which plays an important role in controlling expression of various genes during the transition from logarithmic growth phase to stationary phase or to suppress expression of dlt genes involved in addition of D-alanine to teichoic acid present in the cell wall and the cell membrane, productivity of the protein or polypeptide of interest is considerably improved, as compared with the case of a microorganism strain which has not undergone such a modification.

The recombinant microorganism of the present invention has improved productivity of a protein or polypeptide of interest. Therefore, when a protein or polypeptide of interest is produced by use of the recombinant microorganism, the time and cost required for the production of the protein or polypeptide can be reduced.

In the present invention, identity between amino acid sequences and that between nucleotide sequences are both determined through the Lipman-Pearson method (Science, 227, 1435 (1985)). Specifically, identity is calculated through analysis by use of a homology analysis (search homology) program of genetic information processing software Genetyx-Win (Software Development Co., Ltd.), with ktup (unit size to compare) being set to 2.

As used herein, the term "transcription initiation regulatory region" refers to a region including a promoter and a transcription initiation site; and the term "ribosome-binding site" refers to a site corresponding to the Shine-Dalgarno (SD) sequence (Proc. Natl. Acad. Sci. USA 71, 1342 (1974)) which forms a translation initiation regulatory region together with a start codon.

No particular limitation is imposed on the parental microorganism for constructing the recombinant microorganism of the present invention, so long as it has a *Bacillus subtilis* abrB gene, dltA gene, dltB gene, dltC gene, dltD gene or dltE gene, or a gene corresponding thereto. The parental microorganism may be a wild-type or mutant strain. Specific examples of the parental microorganism include bacteria belonging to the genus *Bacillus*, bacteria belonging to the genus *Clostridium*, and yeast. Of these, bacteria belonging to the genus *Bacillus* are preferred. *Bacillus subtilis* is more preferred, from the viewpoint that complete genomic information of this microorganism has already been obtained, and thus genetic engineering techniques and genomic engineering techniques have been established, and that the microorganism has ability to secrete a produced protein extracellularly.

The names of *Bacillus subtilis* genes and gene regions described herein conform with the *Bacillus subtilis* genome data reported in Nature, 390, 249-256 (1997) and made public by JAFAN (Japan Functional Analysis Network for *Bacillus subtilis*; BSORF DB) on the Internet (bacillus.genome.ad.jp, renewed Mar. 10, 2004).

As used herein, "*Bacillus subtilis* prsA gene" refers to a gene consisting of the nucleotide sequence of SEQ ID NO: 1, and "gene corresponding to the *Bacillus subtilis* prsA gene" refers to a gene having substantially the same function as the *Bacillus subtilis* prsA gene; for example, the prsA gene of *Bacillus licheniformis*, *Bacillus anthracis*, *Bacillus cereus*, *Bacillus thuringiensis*, or *Oceanobacillus iheyensis*, which gene has been generally identified through genomic analysis. Some bacteria including *Bacillus anthracis* have three identified prsA genes. Other examples of the gene corresponding to the *Bacillus subtilis* prsA gene include the following genes (1) to (4).

(1) A gene consisting of a DNA fragment which consists of a nucleotide sequence having an identity of 90% or higher, preferably 95% or higher, more preferably 99% or higher to the nucleotide sequence of SEQ ID NO: 1, and which encodes a protein functionally equivalent to a protein having the amino acid sequence of SEQ ID NO: 2.

(2) A gene consisting of a DNA fragment which hybridizes, under stringent conditions, with a DNA fragment consisting of a nucleotide sequence complementary to the nucleotide sequence of SEQ ID NO: 1, and which encodes a protein functionally equivalent to a protein having the amino acid sequence of SEQ ID NO: 2. The expression "under stringent conditions" refers to, for example, the case where hybridization is carried out through the method described in Molecular Cloning—A LABORATORY MANUAL THIRD EDITION [Joseph Sambrook, David W. Russell., Cold Spring Harbor Laboratory Press]; specifically, the case where hybridization is carried out in a solution containing 6×SSC (composition of 1×SSC: 0.15M sodium chloride, 0.015M sodium citrate, pH 7.0), 0.5% SDS, 5×Denhardt's solution, and 100 mg/mL herring sperm DNA together with a probe constantly at 65° C. for 8 to 16 hours.

(3) A gene consisting of a DNA fragment encoding a protein which consists of an amino acid sequence having an identity of 90% or higher, preferably 95% or higher, more preferably 99% or higher to the amino acid sequence of SEQ ID NO: 2, and which is functionally equivalent to a protein consisting of the amino acid sequence of SEQ ID NO: 2.

(4) A gene consisting of a DNA fragment encoding a protein which consists of an amino acid sequence equivalent to that defined by SEQ ID NO: 2, except that one or more amino acid residues are deleted, substituted, or added, and which is functionally equivalent to a protein consisting of the amino acid sequence of SEQ ID NO: 2.

Examples of the amino acid sequence equivalent to that defined by SEQ ID NO: 2, except that one or more amino acid residues are deleted, substituted, or added include an amino acid sequence equivalent to that defined by SEQ ID NO: 2, except that one to several amino acid residues, preferably 1 to 10 amino acid residues are deleted, substituted, or added. Examples of the addition of amino acid residue(s) include an addition of one to several amino acid residues to both ends of an amino acid sequence.

As used herein, "protein functionally equivalent to a protein consisting of the amino acid sequence of SEQ ID NO: 2" refers to a protein which is considered to have substantially the same function as a protein encoded by the prsA gene, and which is considered to have a chaperone-like function of facilitating folding of the protein which has been transported to the outside of the cytoplasm through the cell membrane.

No particular limitation is imposed on the transcription initiation regulatory region that functions in the microorganism of the present invention or both the transcription initiation regulatory region and the ribosome-binding site that functions in the microorganism of the present invention, so long as the region or both the region and site can function as a transcription initiation regulatory region or a transcription initiation regulatory region and ribosome-binding site in the microorganism serving as a host. However, preferably, the transcription initiation regulatory region that functions in the microorganism, or both the transcription initiation regulatory region and the ribosome-binding site that functions in the microorganism are, for example, a transcription initiation regulatory region or a transcription initiation regulatory region and ribosome-binding site located upstream of a *Bacillus subtilis* spoVG gene or aprE gene or a gene corresponding thereto. Examples of the transcription initiation regulatory region of the *Bacillus subtilis* spoVG gene include a region consisting of a nucleotide sequence represented by nucleotide numbers 38 to 210 of SEQ ID NO: 9; and a region which has a nucleotide sequence homologous to the nucleotide sequence and which functions as the transcription initiation regulatory region. Examples of the transcription initiation regulatory region and ribosome-binding site of the *Bacillus subtilis* spoVG gene include a region consisting of a nucleotide sequence represented by nucleotide numbers 38 to 230 of SEQ ID NO: 9; and a region which has a nucleotide sequence homologous to the nucleotide sequence and which functions as the transcription initiation regulatory region and ribosome-binding site.

In introduction of the transcription initiation regulatory region that functions in the microorganism, or both the transcription initiation regulatory region and the ribosome-binding site that functions in the microorganism into the upstream of the prsA gene or a gene corresponding thereto in the genome of the parental microorganism, the original transcription initiation regulatory region, or the original transcription initiation regulatory region and ribosome-binding site of the *Bacillus subtilis* prsA gene or a gene corresponding thereto may be partially or completely substituted. Alternatively, the original transcription initiation regulatory region, or the original transcription initiation regulatory region and ribosome-binding site may be maintained, and the transcription initiation regulatory region that functions in the microorganism, or both the transcription initiation regulatory region and the ribosome-binding site that functions in the microorganism are additionally inserted.

Substitution of the transcription initiation regulatory region that functions in the microorganism or both the transcription initiation regulatory region and the ribosome-binding site that functions in the microorganism may be carried out through, for example, a known technique employing homologous recombination. Specifically, firstly, through a known technique such as SOE-PCR (SOE: splicing by overlap extension) (Gene, 77, 61, 1989), a drug-resistant gene fragment and a DNA fragment including a region upstream of the original transcription initiation regulatory region of the prsA gene are ligated to the upstream of a DNA fragment including the transcription initiation regulatory region that functions in the microorganism or both the transcription initiation regulatory region and the ribosome-binding site that functions in the microorganism; and a DNA fragment including the entirety or a portion of the translation initiation regulatory region and structural gene region of the prsA gene, or including the entirety or a portion of the structural gene region of the prsA gene is ligated to the downstream of the DNA fragment including the transcription initiation regulatory region that functions in the microorganism or both the transcription initiation regulatory region and the ribosome-binding site that functions in the microorganism. Thus, there is prepared a DNA fragment in which the aforementioned fragments are ligated together in the following sequence: the DNA fragment including the region upstream of the original transcription initiation regulatory region of the prsA gene; the drug-resistant gene fragment; the DNA fragment including the transcription initiation regulatory region that functions in the microorganism or both the transcription initiation regulatory region and the ribosome-binding site that functions in the microorganism; and the DNA fragment including the entirety or a portion of the translation initiation regulatory region and structural gene region of the prsA gene, or including the entirety or a portion of the structural gene region of the prsA gene.

Subsequently, when the thus-prepared DNA fragment is introduced into cells of a parental microorganism through a known technique, double crossover homologous recombination occurs at two regions; i.e., a region upstream of the original transcription initiation regulatory region of the prsA gene in the genome of the parental microorganism, and a region including the entirety or a portion of the translation initiation regulatory region and structural gene region of the prsA gene, or including the entirety or a portion of the structural gene region of the prsA gene. By use of the aforementioned drug-resistant gene as an indicator, there can be isolated a transformant in which the original transcription initiation regulatory region or both the original transcription initiation regulatory region and ribosome-binding site have been substituted by the transcription initiation regulatory region that functions in the microorganism or both the transcription initiation regulatory region and the ribosome-binding site that functions in the microorganism. Thus, the transcription initiation regulatory region that functions in the microorganism or both the transcription initiation regulatory region and the ribosome-binding site that functions in the microorganism, which have been introduced to the upstream of the prsA gene in the genome of the parental microorganism, are maintained in a genetically stable manner. Specific examples of the known technique for introducing a DNA fragment for the gene transfer into a host microorganism include the competent cell transformation method (J. Bacteriol. 93, 1925 (1967)), the protoplast transformation method (Mol. Gen. Genet. 168, 111 (1979)), and electroporation (FEMS Microbiol. Lett. 55, 135 (1990)). The competent cell transformation method is preferred. As used herein, the expression "upstream or downstream of a gene" does not refer to a region as viewed from a replication origin. Specifically, "upstream of a gene or gene region of interest" refers to a region located on the 5'-side of the gene or gene region, and "downstream of a gene or gene region of interest" refers to a region located on the 3'-side of the gene or gene region.

Particularly when *Bacillus subtilis* is employed as a host for producing the recombinant microorganism of the present invention, for example, the method described in Mol. Gen.

Genet., 223, 268, 1990 may be employed for substitution of the original transcription initiation regulatory region or the original transcription initiation regulatory region and ribosome-binding site of the prsA gene with the transcription initiation regulatory region or the transcription initiation regulatory region and ribosome-binding site of the spoVG gene using homologous recombination.

Insertion of the transcription initiation regulatory region that functions in the microorganism or both the transcription initiation regulatory region and the ribosome-binding site that functions in the microorganism may be carried out in a manner similar to the aforementioned substitution procedure by appropriately selecting sequences of DNA fragments which are added to both ends of the transcription initiation regulatory region that functions in the microorganism or both the transcription initiation regulatory region and the ribosome-binding site that functions in the microorganism. For example, a drug-resistant gene fragment and a DNA fragment including a region upstream of the original transcription initiation regulatory region are ligated to the upstream of the transcription initiation regulatory region that functions in the microorganism; and a DNA fragment including the entirety or a portion of the original transcription initiation regulatory region is ligated to the downstream of the transcription initiation regulatory region that functions in the microorganism. Thus, there is prepared a DNA fragment in which the aforementioned fragments and region are ligated together in the following sequence: the DNA fragment including a region upstream of the original transcription initiation regulatory region; the drug-resistant gene fragment; the transcription initiation regulatory region that functions in the microorganism; and the DNA fragment including the entirety or a portion of the original transcription initiation regulatory region. Subsequently, the thus-prepared DNA fragment is inserted in a host microorganism, and then the resultant transformant is isolated by use of the drug-resistant gene as an indicator. In the genome of the thus-isolated transformant, the original transcription initiation regulatory region and the transcription initiation regulatory region that functions in the microorganism are stably maintained such that the regions are adjacent to each other.

In the present invention, no particular limitation is imposed on the upstream region in the genome of a host microorganism to which the transcription initiation regulatory region that functions in the microorganism or both the transcription initiation regulatory region and the ribosome-binding site that functions in the microorganism are introduced, so long as the upstream region is located upstream of the start codon of the prsA gene. However, the upstream region is preferably a region located within 2,000 base pairs or less, more preferably 500 base pairs or less, still more preferably 100 base pairs or less, even more preferably 50 base pairs or less, upstream of the aforementioned start codon.

In the present invention, a gene fragment prepared by ligating the transcription initiation regulatory region that functions in the microorganism or both the transcription initiation regulatory region and the ribosome-binding site that functions in the microorganism to the upstream of the *Bacillus subtilis* prsA gene may be prepared by ligating a fragment of the transcription initiation regulatory region that functions in the microorganism or both the transcription initiation regulatory region and the ribosome-binding site that functions in the microorganism to a fragment of the prsA gene through a known technique such as the restriction enzyme method, or SOE-PCR (SOE: splicing by overlap extension) (Gene, 77, 61, 1989)). The fragments may be obtained through a known cloning technique such as PCR using the genome of *Bacillus subtilis* or another microorganism as a template. The thus-prepared gene fragment may be introduced into the cytoplasm by use of a vector such as plasmid. Alternatively, the gene fragment may be introduced into the chromosome of a host cell by homologous recombination between the chromosome and the nucleic acid fragment introduced into the cell through a known transformation technique.

The region of the chromosome of a host into which such a fragment is introduced is preferably a region in a nonessential gene, or a region in a nongenic region upstream of a nonessential gene. Specific examples include a region in an aprE gene, an sacB gene, an nprE gene, an amyE gene, or a ybxG gene; and a region in a nongenic region upstream of such a nonessential gene. A region in an amyE gene, or a region in a nongenic region upstream of a ybxG gene is preferred. As used herein, the term "nonessential gene" refers to a gene which, even when disrupted, allows a host to survive at least under certain conditions. Deletion of the entirety or a portion of a nonessential gene or a nongenic region upstream of the gene, which would otherwise occur in association with the fragment introduction, does not cause any problem.

Next will be specifically described a method for introducing a gene fragment prepared by ligating a transcription initiation regulatory region that functions in the microorganism or both the transcription initiation regulatory region and a ribosome-binding site that functions in the microorganism to the upstream of the prsA gene into the genome of a parental microorganism using double crossover method, the method employing a DNA fragment prepared through SOE-PCR (SOE: splicing by overlap extension) (Gene, 77, 61, 1989).

The DNA fragment employed in this method for the gene transfer is a DNA fragment including a fragment of about 0.1 to about 3 kb, preferably 0.4 to 3 kb locating adjacent upstream to the introduction site in the genome of a parental microorganism (hereinafter the fragment may be referred to as "fragment (1)"); a fragment of about 0.1 to about 3 kb, preferably 0.4 to 3 kb locating adjacent downstream to the introduction site (hereinafter the fragment may be referred to as "fragment (2)"); a fragment including a transcription initiation regulatory region that functions in the microorganism or both the transcription initiation regulatory region and a ribosome-binding site that functions in the microorganism (hereinafter the fragment may be referred to as "fragment (3)"); a fragment of the prsA gene (hereinafter the fragment may be referred to as "fragment (4)"); and a fragment of a drug-resistant marker gene (hereinafter the fragment may be referred to as "fragment (5)"), wherein fragments (3), (4), and (5) are inserted between fragments (1) and (2). In the first cycle of PCR, the aforementioned five fragments (1) to (5) are prepared.

The primers employed in this step are, for example, those designed so that an upstream 10-30 base pair sequence of fragment (3) is added to the downstream end of fragment (1); a downstream 10-30 base pair sequence of fragment (3) is added to the upstream end of fragment (4); an upstream 10-30 base pair sequence of fragment (5) is added to the downstream end of fragment (4); and a downstream 10-30 base pair sequence of fragment (5) is added to the upstream side of fragment (2) (FIG. 1).

Subsequently, by using, as templates, the five PCR fragments prepared in the first cycle, the second cycle of PCR is carried out by use of an upstream primer of fragment (1) and a downstream primer of fragment (2). This step causes annealing of fragment (3) with the fragment (3) sequence added to the downstream end of fragment (1); annealing of fragment (3) with the fragment (3) sequence added to the upstream end of fragment (4); annealing of fragment (5) with the fragment (5) sequence added to the downstream end of fragment (4); and annealing of fragment (5) with the fragment (5) sequence added to the upstream side of fragment (2). Through PCR amplification, there can be obtained a DNA fragment including fragments (1) to (5), wherein fragment (1), fragment (3), fragment (4), fragment (5), and fragment (2) are ligated in this sequence (FIG. 1).

The drug-resistant marker gene employed may be, for example, an erythromycin-resistant gene. The aforementioned PCR may be carried out under typical conditions described in literature (see, for example, PCR Protocols. Current Methods and Applications, Edited by B. A. White, Humana Press, pp. 251, 1993, Gene, 77, 61, 1989) by use of a primer set shown in Table 1 and a generally used enzyme kit for PCR, such as Pyrobest DNA Polymerase (product of Takara Shuzo).

When the thus-obtained DNA fragment for the gene transfer is introduced into cells through the competent method or a similar method, intracellular genetic recombination occurs in homologous regions which are present upstream and downstream of the introduction site in the genome having sequential identity. Thus, cells into which the gene fragment prepared by ligating the functional transcription initiation regulatory region or the functional transcription initiation regulatory region and ribosome-binding site to the upstream of the prsA gene has been introduced can be selectively separated by use of a drug-resistant marker. In selective separation by use of a drug-resistant marker, for example, colonies which have grown on an agar medium containing erythromycin are separated, followed by selection of cells through PCR or a similar technique employing the genome as a template, in which introduction of the gene fragment in the genome is confirmed. No particular limitation is imposed on the aforementioned drug-resistant marker gene, so long as it can be employed for cell selection by use of a common antibiotic. Examples of the drug-resistant marker gene which may employed include, in addition to an erythromycin-resistant gene, drug-resistant marker genes such as a chloramphenicol-resistant gene, a neomycin-resistant gene, a spectinomycin-resistant gene, a tetracycline-resistant gene, and a brasticidin S-resistant gene.

In the recombinant microorganism of the present invention, in addition to the aforementioned enhancement of expression of the prsA gene for overexpression of PrsA, one or more genes selected from among an abrB gene, a dltA gene, a dltB gene, a dltC gene, a dltD gene, a dltE gene, and a gene corresponding thereto are deleted or inactivated. Deletion or inactivation of the abrB gene among these genes is a modification for altering expression of various genes involved in, for example, sporulation, competence, or nutrition acquisition. Deletion or inactivation of dlt genes is a modification for suppressing addition of D-alanine to teichoic acid present in the cell wall and the cell membrane. In deletion or inactivation of dlt genes, the aforementioned dlt genes may be deleted or inactivated singly or in combination of a plurality of species. For example, the dltB gene or the dltD gene may be deleted or inactivated singly, or the dltA, dltB, dltC, dltD, and dltE genes may be deleted or inactivated in combination.

In deletion or inactivation of the aforementioned genes, the genes may be deleted or inactivated singly or in combination of two or more species. In addition to deletion or inactivation of the aforementioned genes, expression of a gene other than the genes may be enhanced, or the gene may be deleted or inactivated. The expression "deletion or inactivation of a gene" encompasses substitution or deletion of the entirety or a portion of the nucleotides of the gene, and insertion of a nucleotide(s) in the gene.

In the present invention, the gene deleted or inactivated is preferably the abrB gene, the dltB gene, the dltD gene and the dltABCDE genes, or a gene(s) corresponding thereto.

In *Bacillus subtilis*, the abrB gene encodes a transcription factor which plays an important role in controlling expression of various genes involved in, for example, sporulation, competence, or nutrition acquisition during the transition from logarithmic growth phase to stationary phase.

In *Bacillus subtilis*, the dltA, dltB, dltC, dltD, and dltE genes belong to the same operon, and these genes are involved in addition of D-alanine to teichoic acid present in the cell wall and the cell membrane.

Table 4 summarizes the gene numbers and functions of the *Bacillus subtilis* abrB gene, dltA gene, dltB gene, dltC gene, dltD gene, and dltE gene.

As used herein, "gene corresponding to the *Bacillus subtilis* abrB gene, dltA gene, dltB gene, dltC gene, dltD gene, or dltE gene" refers to a gene having substantially the same function as the abrB, dltA, dltB, dltC, dltD, or dltE gene; for example, a gene which is derived from a microorganism other than *Bacillus subtilis*, preferably, originally present in the genome of a bacterium belonging to the genus *Bacillus*, and which has a nucleotide sequence having an identity of 70% or higher, preferably 80% or higher, more preferably 90% or higher, still more preferably 95% or higher, even more preferably 98% or higher to the nucleotide sequence of the abrB, dltA, dltB, dltC, dltD, or dltE gene. The degree of identity between nucleotide sequences is determined through the Lipman-Pearson method (Science, 227, 1435, 1985).

In an example procedure for deleting or inactivating any of the aforementioned genes, the gene (target gene) may be specifically deleted or inactivated, or alternatively, randomized deletion or inactivating mutation of genes may be performed, followed by evaluation of protein productivity and gene analysis through an appropriate method.

Figure 3:
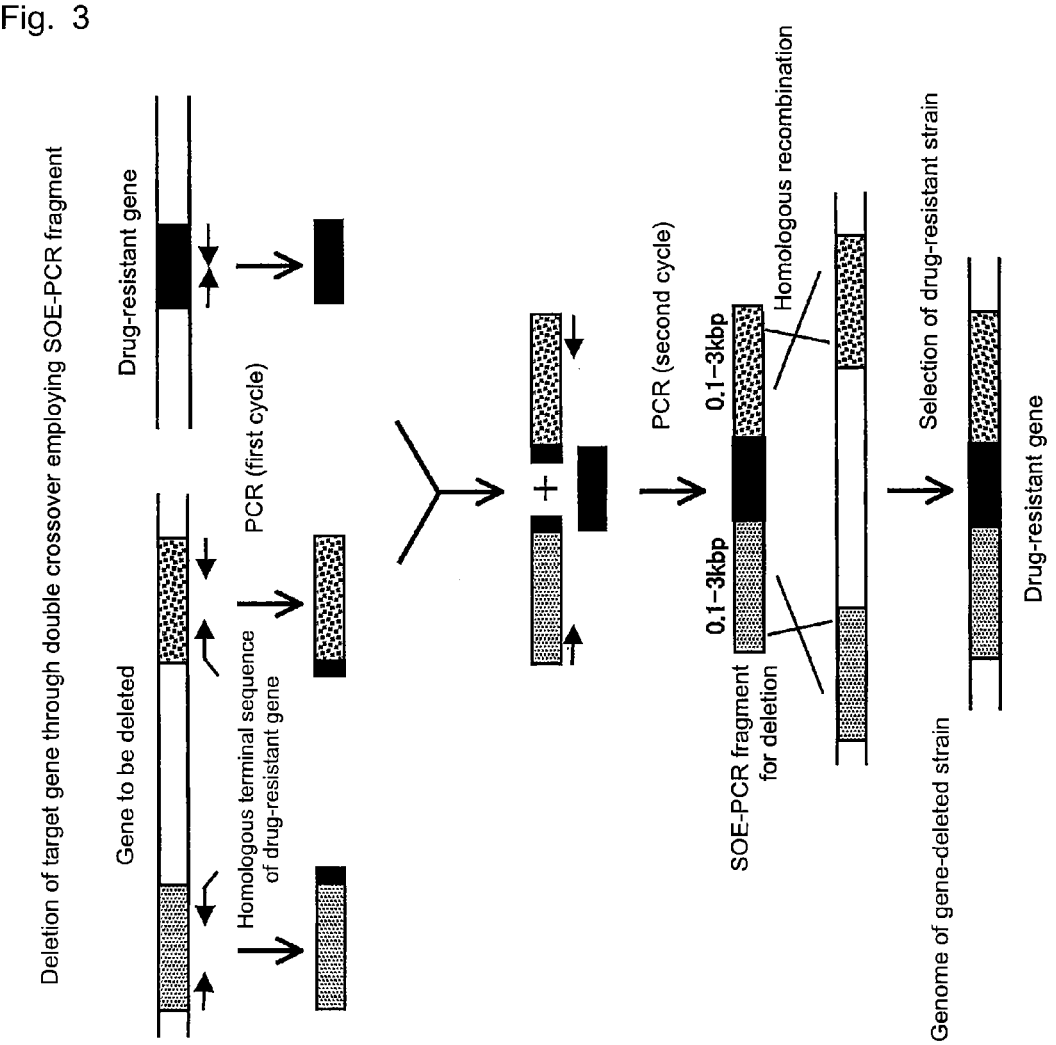
FIG. 3 schematically shows deletion of a target gene through double crossover employing an SOE-PCR fragment.

Deletion or inactivation of the target gene may be carried out through, for example, homologous recombination. Specifically, inactivation of the target gene may be performed through the following procedure: a DNA fragment including a portion of the target gene is cloned with an appropriate plasmid vector, to thereby prepare a circular recombinant plasmid; the recombinant plasmid is introduced into cells of a parent microorganism; and the target gene in the genome of the parent microorganism is cleaved through homologous recombination effected in a partial region of the target gene. Alternatively, the following procedure may be carried out: the target gene is inactivated through mutation such as substitution or insertion of a base, or a linear DNA fragment including regions upstream and downstream of the target gene but not including the target gene such as a linear DNA fragment shown in FIG. 3 is constructed through PCR or a similar technique; the thus-engineered gene or fragment is introduced into cells of a parent microorganism; and double cross-over homologous recombination is caused to occur at two sites outside the mutation site within the target gene in the genome of the parent microorganism, or at two regions upstream and downstream of the target gene, to thereby substitute the target gene in the genome with a deleted or inactivated gene fragment.

Particularly when the parent microorganism employed for construction of the recombinant microorganism of the present invention is *Bacillus subtilis*, since several reports have already described methods for deleting or inactivating the target gene through homologous recombination (see, for example, Mol. Gen. Genet., 223, 268, 1990), the host microorganism of the present invention can be produced through such a method.

Randomized gene deletion or inactivation may be carried out through a method similar to the aforementioned homologous recombination method by use of a randomly cloned DNA fragment, or a conventional method such as irradiation of a parent microorganism with γ-rays or similar rays.

Next will be described in more detail a deletion method employing double crossover by use of a DNA fragment designed for the deletion purpose, the DNA fragment being prepared through SOE-PCR (SOE: splicing by overlap extension) (Gene, 77, 61, 1989). However, in the present invention, the method for deleting genes is not limited to the below-described method.

The DNA fragment employed in this method for the deletion purpose is a fragment prepared by inserting a drug-resistant marker gene fragment between a fragment of about 0.1 to about 3 kb, preferably 0.4 to 3 kb locating adjacent upstream to a gene to be deleted, and a fragment of about 0.1 to about 3 kb, preferably 0.4 to 3 kb locating adjacent downstream to the gene. In the first cycle of PCR, the following three fragments are prepared: the fragment upstream to the gene to be deleted, the fragment downstream to the gene to be deleted and the drug-resistant marker gene fragment. The primers employed in this step are, for example, those designed so that an upstream 10-30 base pair sequence of the drug-resistant marker gene is added to the downstream end of the fragment upstream to the gene to be deleted, whereas a downstream 10-30 base pair sequence of the drug-resistant marker gene is added to the upstream end of the fragment downstream to the gene to be deleted (FIG. 3).

Subsequently, by using, as templates, the three PCR fragments prepared in the first cycle, the second cycle of PCR is carried out by use of an upstream primer of the fragment upstream to the gene to be deleted and a downstream primer of the fragment downstream to the gene to be deleted. This step causes annealing of the drug-resistant marker gene fragment in the drug-resistant marker gene sequence added to the downstream end of the fragment upstream to the gene to be deleted and to the upstream end of the fragment downstream to the gene to be deleted. Through PCR amplification, there can be obtained a DNA fragment including the drug-resistant marker gene inserted between the fragment upstream to the gene to be deleted and the fragment downstream to the gene to be deleted (FIG. 3).

When a chloramphenicol-resistant gene is employed as the drug-resistant marker gene, a DNA fragment for deleting a target gene can be obtained through SOE-PCR under typical conditions described in literature (see, for example, PCR Protocols. Current Methods and Applications, Edited by B. A. White, Humana Press, pp. 251 (1993), Gene, 77, 61, 1989), by use of, for example, a primer set shown in Table 1 and a conventional enzyme kit for PCR, such as Pyrobest DNA Polymerase (product of Takara Shuzo).

When the thus-obtained DNA fragment for gene deletion is introduced into cells through the competent method or a similar method, intracellular genetic recombination occurs in homologous regions which are present upstream and downstream of the gene to be deleted having sequential identity. Thus, cells in which the target gene has been substituted with a drug-resistant gene can be selectively separated by use of the drug-resistant marker. Specifically, when a DNA fragment for gene deletion prepared by use of a primer set shown in Table 1 is introduced into cells, colonies which have grown on an agar culture medium containing chloramphenicol are separated, and substitution of the target gene in the genome with the chloramphenicol-resistant gene is confirmed through, for example, a PCR technique employing the genome as a template.

The recombinant microorganism of the present invention can be produced by transferring a gene encoding a protein or polypeptide of interest into the thus-genetically modified microorganism. As used herein, the expression "protein or polypeptide of interest" refers to a protein or polypeptide which is intended to be produced or purified. As used herein, the term "gene" of "a microorganism having a gene encoding a protein or polypeptide of interest" encompasses a gene which is intrinsic to the microorganism, and a gene which is not intrinsic to the microorganism, i.e. a foreign gene.

No particular limitation is imposed on the protein or polypeptide of interest, and examples thereof include bioactive peptides and enzymes for industrial uses such as detergents, foods, textile, feeds, chemicals, medicine, and diagnosis. The protein or polypeptide of interest is preferably an industrial enzyme. Industrial enzymes may be functionally grouped into, for example, oxidoreductases, transferases, hydrolases, lyases, isomerases, and ligases/synthetases. Examples of preferred industrial enzymes include hydrolases such as cellulase, α-amylase, and protease. Examples of α-amylase include α-amylases derived from microorganisms, preferably derived from bacteria belonging to the genus Bacillus, more preferably derived from Bacillus sp. KSM-K38 strain. Specific examples of α-amylase derived from Bacillus sp. KSM-K38 strain include alkaline amylase derived from a bacterium belonging to the genus Bacillus and consisting of an amino acid sequence represented by amino acid residue numbers 1 to 480 of SEQ ID NO: 4, and amylase consisting of an amino acid sequence having an identity of 70% or higher, preferably 80% or higher, more preferably 90% or higher, still more preferably 95% or higher, even more preferably 98% or higher to the aforementioned amino acid sequence. The cellulase is, for example, cellulase belonging to family 5 in the classification of polysaccharide hydrolase (Biochem. J., 280, 309, 1991); preferably, cellulase derived from a microorganism, more preferably cellulase derived from a bacterium belonging to the genus Bacillus. Specific examples of the cellulase include alkaline cellulases derived from Bacillus sp. KSM-S237 strain (FERM BP-7875) and Bacillus sp. KSM-64 strain (FERM BP-2886). Examples of more preferred cellulases include alkaline cellulase derived from a bacterium belonging to the genus Bacillus and consisting of an amino acid sequence represented by amino acid residue numbers 1 to 795 of SEQ ID NO: 6; alkaline cellulase derived from a bacterium belonging to the genus Bacillus and consisting of an amino acid sequence represented by amino acid residue numbers 1 to 793 of SEQ ID NO: 8; and cellulase consisting of an amino acid sequence having an identity of 70% or higher, preferably 80% or higher, more preferably 90% or higher, still more preferably 95% or higher, even more preferably 98% or higher to any of the aforementioned amino acid sequences. The protease is, for example, serine protease and metalloprotease which are derived from microorganisms; preferably, bacteria belonging to the genus Bacillus.

A gene for a protein or polypeptide of interest to be transferred to the recombinant microorganism of the present invention preferably has one or more regulatory regions relating to transcription, translation and secretion of the gene, which region(s) is(are) specifically one or more regions selected from a transcription initiation regulatory region including a promoter and a transcription initiation site; a translation initiation regulatory region including a ribosome-binding site and a start codon; and a secretion signal peptide region, properly ligated to the upstream thereof. Preferably, the following three regions; i.e., the transcription initiation regulatory region, the translation initiation regulatory region, and the secretion signal region, are ligated to the gene for the protein or polypeptide of interest. More preferably, the secretion signal peptide region is derived from a cellulase gene of a bacterium belonging to the genus *Bacillus*; the transcription initiation regulatory region and the translation initiation regulatory region are each derived from a 0.6 to 1 kb region upstream of the cellulase gene; and these regions are properly ligated to the gene for the protein or polypeptide of interest.

For example, preferably, a transcription initiation regulatory region, a translation initiation regulatory region, and a secretion signal peptide region of a cellulase gene derived from a bacterium belonging to the genus *Bacillus*, namely KSM-S237 strain (FERM BP-7875) and KSM-64 strain (FERM BP-2886), disclosed in, for example, JP-A-2000-210081 or JP-A-1992-190793, are properly ligated to a structural gene for a protein or polypeptide of interest. More specifically, a structural gene for a protein or polypeptide of interest is preferably ligated properly to a DNA fragment consisting of a nucleotide sequence represented by nucleotide numbers 1 to 659 of SEQ ID NO: 5; a DNA fragment having a nucleotide sequence represented by nucleotide numbers 1 to 696 of SEQ ID NO: 7; a DNA fragment consisting of a nucleotide sequence having an identity of 70% or higher, preferably 80% or higher, more preferably 90% or higher, still more preferably 95% or higher, even more preferably 98% or higher to any of the aforementioned nucleotide sequences; or a DNA fragment consisting of a nucleotide sequence obtained through partial deletion, substitution, or addition of any of the aforementioned nucleotide sequences.

As used herein, "DNA fragment consisting of a nucleotide sequence obtained through partial deletion, substitution, or addition of any of the aforementioned nucleotide sequences" refers to a DNA fragment in which a portion of any of the aforementioned nucleotide sequences has undergone deletion, substitution, or addition, but which maintains functions involving transcription, translation and secretion of the gene.

Transfer of such a gene encoding a protein or polypeptide of interest may be carried out through, for example, (1) transfer by use of a vector, or (2) insertion in the genome of a host. When (1) gene transfer by use of a vector is carried out, a vector containing a gene encoding a protein or polypeptide of interest, which gene has one or more regulatory regions involving to transcription, translation and secretion of the gene, which region(s) is (are) specifically one or more regions selected from a transcription initiation regulatory region including a promoter and a transcription initiation site; a translation initiation regulatory region including a ribosome-binding site and a start codon; and a secretion signal peptide region, properly ligated the upstream thereof, is introduced into the host through an appropriate transformation technique such as the competent cell transformation method, the protoplast transformation method, or electroporation. No particular limitation is imposed on the vector employed, so long as it is an appropriate carrier of a nucleic acid molecule which transfers a gene of interest to a host for amplification and expression. Examples of the vector include plasmid; artificial chromosomes such as YAC and BAC; vectors using transposon; and cosmid. Examples of the plasmid include pUB110 and pHY300PLK.

(2) Insertion in the genome of a host may be carried out through, for example, homologous recombination. Specifically, a DNA fragment prepared by ligating a gene encoding a protein or polypeptide of interest to a portion of a chromosomal region to which the gene is transferred is introduced into cells of a microorganism, to thereby allow homologous recombination to occur in a portion of the chromosomal region. Thus, the gene can be integrated into the genome of the microorganism.

No particular limitation is imposed on the chromosomal region to which the gene is transferred, but the chromosomal region is preferably a nonessential gene region, or a nongenic region upstream of a nonessential gene region.

Production of a protein or polypeptide of interest by use of the recombinant microorganism of the present invention may be carried out in such a manner that cells of the microorganism are inoculated into a culture medium containing assimilable carbon sources and nitrogen sources, and other essential components; the cells are cultured through a common microorganism culturing method; and, after completion of culturing, the resultant protein or polypeptide is collected and purified. As described in the Examples hereinbelow, the productivity of the protein or polypeptide of interest is improved, as compared with the case where a microorganism which has not undergone the aforementioned genetic modification is employed.

Next will be described in detail methods for constructing the recombinant microorganism of the present invention and methods for producing amylase by use of the recombinant microorganism.

EXAMPLES

In the Examples described hereinbelow, DNA fragment amplification was carried out through polymerase chain reaction (PCR) by use of GeneAmp PCR System (product of Applied Biosystems), and Pyrobest DNA Polymerase (product of Takara Bio Inc.) and reagents attached thereto. Specifically, PCR was carried out by use of a reaction mixture (total: 50 µL) containing appropriately diluted template DNA (1 µL), a sense primer (20 pmol), an antisense primer (20 pmol), and Pyrobest DNA Polymerase (2.5 U). PCR was carried out through 30 cycles of treatment of the reaction mixture, each cycle consisting of the three steps of thermal treatment: 98° C.×10 seconds; 55° C.×30 seconds; and 72° C.×1 to 5 minutes, which varies depending on a amplification product of interest, approximately 1 minute for 1 kb, followed by treatment of the reaction mixture at 72° C. for five minutes.

In the Examples described hereinbelow, the expression "upstream or downstream of a gene" does not refer to a region as viewed from a replication origin. Rather, "upstream of a gene" refers to a region located on the 5'-side of the start codon of the gene of interest in each procedure or step, and "downstream of a gene" refers to a region located on the 3'-side of the stop codon of the gene of interest in each procedure or step.

The names of genes and gene regions employed in the below-described Examples conform with the *Bacillus subtilis* genome data reported in Nature, 390, 249-256 (1997) and made public by JAFAN (Japan Functional Analysis Network for *Bacillus subtilis*; BSORF DB) on the Internet (bacillus.genome.ad.jp, renewed Mar. 10, 2004).

Transformation of *Bacillus subtilis* was carried out as described below. Specifically, cells of *Bacillus subtilis* were inoculated into an SPI medium (0.20% ammonium sulfate, 1.40% dipotassium hydrogenphosphate, 0.60% potassium dihydrogenphosphate, 0.10% trisodium citrare dihydrate, 0.50% glucose, 0.02% casamino acid (Difco), 5 mM magnesium sulfate, 0.25 µM manganese chloride, and 50 µg/mL tryptophan), followed by shake culturing at 37° C. until the growth level (OD600) reached about 1. After completion of shake culturing, an aliquot of the resultant culture liquid was inoculated into a 9-fold amount of an SPII medium (0.20% ammonium sulfate, 1.40% dipotassium hydrogenphosphate, 0.60% potassium dihydrogenphosphate, 0.10% trisodium citrare dihydrate, 0.50% glucose, 0.01% casamino acid (Difco), 5 mM magnesium sulfate, 0.40 µM manganese chloride, and 5 µg/mL tryptophan), followed by further shake culturing until the growth level (OD600) reached about 0.4, to thereby prepare competent cells of *Bacillus subtilis*.

Subsequently, a solution containing each DNA fragment (e.g., SOE-PCR reaction mixture) (5 µL) was added to the thus-prepared competent cell suspension (SPII-medium-based culture liquid) (100 µL), followed by shake culturing at 37° C. for one hour. Thereafter, the entire amount of the resultant culture liquid was smeared on an LB agar medium (1% triptone, 0.5% yeast extract, 1% NaCl, and 1.5% agar) containing an appropriate drug, followed by stationary culturing at 37° C. Thereafter, the thus-grown colonies were separated as a transformant, and the genome of the thus-obtained transformant was extracted. PCR employing the genome as a template indicated that a genomic modification of interest had been achieved.

Introduction of a gene encoding a protein or polypeptide of interest into a host microorganism was carried out through any of the following techniques: the competent cell transformation method (J. Bacteriol. 93, 1925 (1967)), electroporation (FEMS Microbiol. Lett. 55, 135 (1990)), and the protoplast transformation method (Mol. Gen. Genet. 168, 111 (1979)).

Culturing for the production of a protein employing the recombinant microorganism was carried out by use of an LB medium (1% triptone, 0.5% yeast extract, and 1% NaCl), a 2×YT medium (1.6% triptone, 1% yeast extract, and 0.5% NaCl), a 2×L-maltose medium (2% triptone, 1% yeast extract, 1% NaCl, 7.5% maltose, and 7.5 ppm manganese sulfate tetra- to pentahydrate), or a CSL fermentation medium (2% yeast extract, 0.5% corn steep liquor (CSL), 0.05% magnesium chloride heptahydrate, 0.6% urea, 0.2% L-tryptophan, 10% glucose, 0.15% sodium dihydrogenphosphate, and 0.35% disodium hydrogenphosphate; pH 7.2)

Example 1

Construction of Strain Showing Enhanced Expression of prsA Gene

Figure 2:
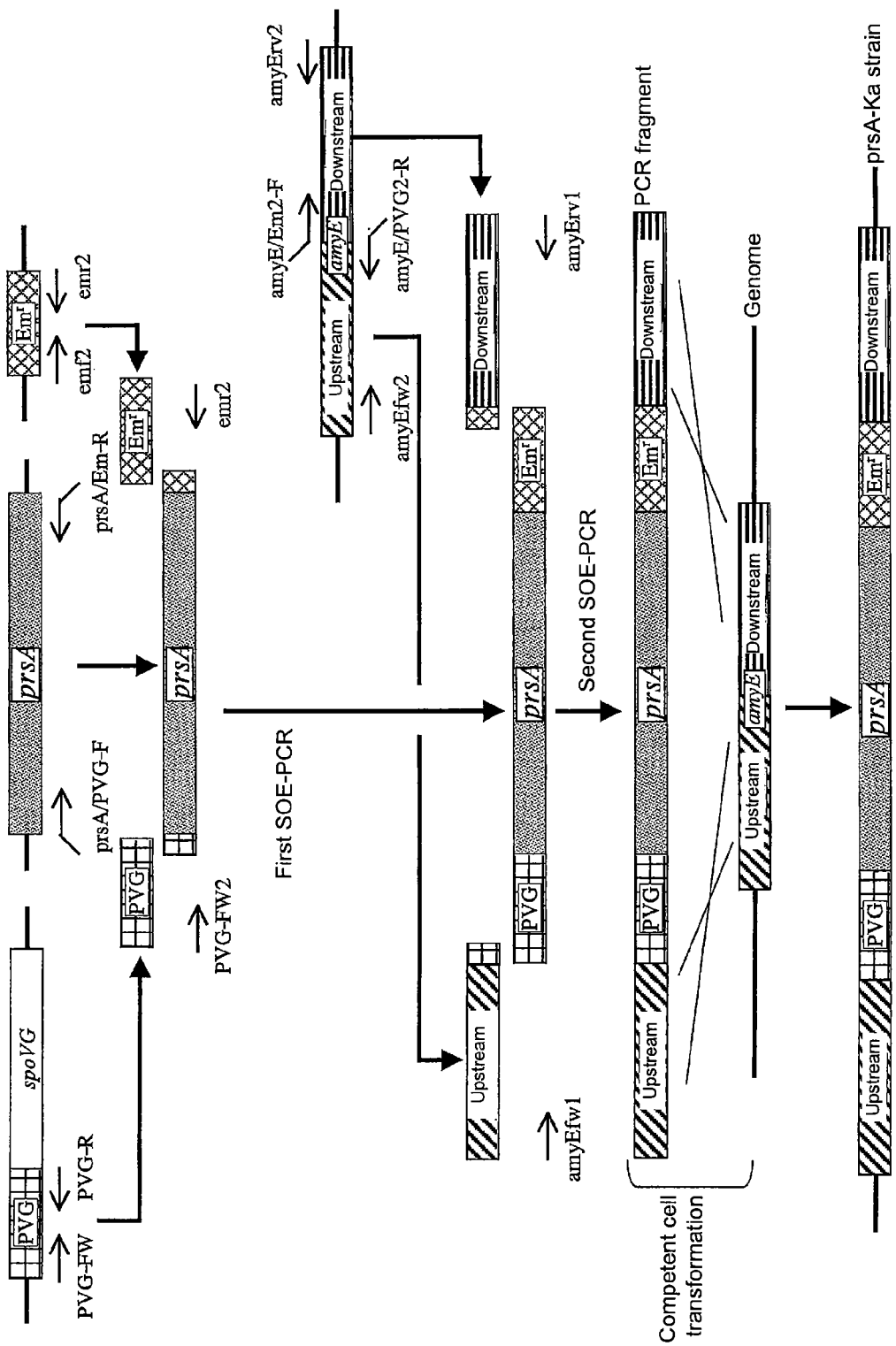
FIG. 2 schematically shows a method for preparing, through SOE-PCR, a DNA fragment for constructing a strain showing enhanced expression of prsA.

A mutant strain showing enhanced expression of the prsA gene was constructed as follows (see FIG. 2). By using, as a template, genomic DNA extracted from *Bacillus subtilis* 168 strain, and two primer sets (PVG-FW and PVG-R, and prsA/PVG-F and prsA/Em2-R) shown in Table 1, a 0.2 kb fragment (A) including the transcription initiation regulatory region and ribosome-binding site of the spoVG gene, and a 0.9 kb fragment (B) including the prsA gene were amplified through PCR. By use of plasmid pMUTIN4 (Microbiology. 144, 3097 (1998)) serving as a template, and a primer set (emf2 and emr2) shown in Table 1, a 1.3 kb fragment (C) including an erythromycin (Em)-resistant gene was amplified through PCR.

Subsequently, SOE-PCR was carried out by use of the thus-obtained three fragments (A), (B), and (C) in combination as templates, and by use of a primer set (PVG-FW2 and emr2) shown in Table 1, to thereby prepare a 2.4 kb DNA fragment (D) in which the three fragments (A), (B), and (C) were ligated in this sequence; the transcription initiation regulatory region and ribosome-binding site of the spoVG gene were ligated to the upstream of the prsA gene so that the start codon of the prsA gene was located at the start codon of the spoVG gene; and the Em-resistant gene was ligated to the downstream of the prsA gene. Subsequently, by using, as a template, genomic DNA extracted from *Bacillus subtilis* 168 strain, and two primer sets (amyEfw2 and amyE/PVG2-R, and amyE/Em2-F and amyErv2) shown in Table 1, a 1.0 kb fragment (E) including the 5'-side region of the amyE gene, and a 1.0 kb fragment (F) including the 3'-side region of the amyE gene were amplified through PCR.

Subsequently, SOE-PCR was carried out by use of the thus-obtained three fragments (E), (F), and (D) in combination as templates, and by use of a primer set (amyEfw1 and amyErv1) shown in Table 1, to thereby prepare a DNA fragment (G) (total length of 4.3 kb) in which the three fragments (E), (D), and (F) were ligated in this sequence; and the 2.4 kb DNA fragment, in which the prsA gene was ligated to the downstream of the transcription initiation regulatory region and ribosome-binding site of the spoVG gene and the Em-resistant gene was ligated to the downstream of the prsA gene, was inserted into the center of the amyE gene.

*Bacillus subtilis* 168 strain was transformed through the competent cell method by use of the thus-obtained 4.3 kb DNA fragment (G), and colonies grown in an LB agar medium containing erythromycin (1 µg/mL) and lincomycin (25 µg/mL) were separated as a transformant. PCR employing, as a template, genomic DNA extracted from the transformant, and two primer sets (amyEfw2 and prsA/Em2-R, and prsA/PVG-F and amyErv2) shown in Table 1 indicated that 2.4 kb and 3.3 kb DNA fragments were amplified, and that the DNA fragment in which the prsA gene was ligated to the downstream of the transcription initiation regulatory region and ribosome-binding site of the spoVG gene was inserted into the amyE gene site in the genome of *Bacillus subtilis* 168 strain. The thus-obtained strain was denominated "prsA-Ka strain."

TABLE 1

| Primer | Nucleotide sequence | SEQ ID NO |
|---|---|---|
| PVG-FW | GTTAGTCGAGATCGAAGTTA | 10 |
| PVG-R | AGTAGTTCACCACCTTTTCC | 11 |
| prsA/PVG-F | GGAAAAGGTGGTGAACTACTATGAAGAAAATCGCAATAGC | 12 |
| prsA/Em2-R | TTTGCACTGATTGGTGTATCTTATTTAGAATTGCTTGAAG | 13 |
| emf2 | GATACACCAATCAGTGCAAA | 14 |
| emr2 | CAAGAGTTTGTAGAAACGCA | 15 |
| PVG-FW2 | TAAGAAAAGTGATTCTGGGA | 16 |

TABLE 1-continued

| Primer | Nucleotide sequence | SEQ ID NO |
|---|---|---|
| amyEfw2 | GGAGTGTCAAGAATGTTTGC | 17 |
| amyE/PVG2-R | TCCCAGAATCACTTTTCTTAATCATCGCTCATCCATGTCG | 18 |
| amyE/Em2-F | TGCGTTTCTACAAACTCTTGGTTTAGGCTGGGCGGTGATA | 19 |
| amyErv2 | TCAATGGGGAAGAGAACC | 20 |
| amyEfw1 | TCAAAACCTCTTTACTGCCG | 21 |
| amyErv1 | CACGTAATCAAAGCCAGGCT | 22 |
| S237ppp-F2 (BamHI) | CCCGGATCCAACAGGCTTATATTTA | 23 |
| S237ppp-R2 (ALAA) | TTCAATCCATCTGCTGCAAGAGCTGCCGG | 24 |
| K38matu-F2 (ALAA) | GCTCTTGCAGCAGATGGATTGAACGGTACG | 25 |
| SP64K38-R (XbaI) | TTGGTCTAGACCCCAAGCTTCAAAGTCGTA | 26 |
| catf | CAACTAAAGCACCCATTAG | 27 |
| catr | CTTCAACTAACGGGGCAG | 28 |
| abrB-FW | TTGATCAATTCAACTGGGTG | 29 |
| abrB/Cm-R | CTAATGGGTGCTTTAGTTGTCTCCTCCCAAGAGATACTT | 30 |
| abrB/Cm-F | CTGCCCCGTTAGTTGAAGAATCATTTCTTGTACAAAAAAC | 31 |
| abrB-RV | TTTCAAAAAACTAACTCGGAA | 32 |
| abrB-FW2 | CAATATCAACGAGCTGAGTT | 33 |
| abrB-RV2 | ATGTTAAGGCGCCAAATGAG | 34 |
| dltB-FW | TAAACCAAGCGCCGTTCTCA | 35 |
| dltB/Cm-R | CTAATGGGTGCTTTAGTTGCAGAAGAAGAATGCCAAGCA | 36 |
| dltB/Cm-F | CTGCCCCGTTAGTTGAAGTTTCTCAGGAAAACCATTTC | 37 |
| dltB-RV | CTTATCCTTTACTGACTGCG | 38 |
| dltB-FW2 | TTTACATTGCGTGACAAAGG | 39 |
| dltB-RV2 | TTCTTTTCCAGCATGCTGTA | 40 |
| dltD-FW | CGACAGATACCGCCGGTTCG | 41 |
| dltD/Cm-R | CTAATGGGTGCTTTAGTTGTGCGAATAGAATAAACGCCA | 42 |
| dltD/Cm-F | CTGCCCCGTTAGTTGAAGGCATCTCATAGGACGCGGCT | 43 |
| dltD-RV | TGTTTAGTCATGGTCAATCT | 44 |
| dltD-FW2 | TATACGGGAATCCATAAAATC | 45 |
| dltD-RV2 | TTCTATTGTATACCTTCAACA | 46 |
| dltA-FW | CCAGCTGCTGCTGGCACAAA | 47 |
| dltA/Cm-R | CTAATGGGTGCTTTAGTTGAGTTATTCTCTCTCCAATTAG | 48 |
| dltE/Cm-F | CTGCCCCGTTAGTTGAAGTTTCTCCTGCTTTTTTCATAT | 49 |
| dltE-RV | ATGACCTCATCGATCGCAAT | 50 |
| dltA-FW2 | AAAATCGTTTTAGGCTTCATT | 51 |
| dltE-RV2 | AATTGCGCGTAATGCCTTCC | 52 |
| Bce/PVG-F | GGAAAAGGTGGTGAACTACTATGAAGAAAGCTATGCTTGCCT | 53 |
| Bce/emf2-R | GCACTGATTGGTGTATCTTATTTCTTTTCTTCTTTTTTATCGTCA | 54 |

Example 2

Evaluation of Secretion/Production of Alkaline Amylase—1

As described below, heterologous protein productivity of the prsA-Ka strain obtained in Example 1 was evaluated on the basis of productivity of alkaline amylase derived from a bacterium belonging to the genus *Bacillus* and consisting of the amino acid sequence of SEQ ID NO: 4.

A 1.5 kb DNA fragment (H) encoding alkaline amylase (JP-A-2000-184882, Eur. J. Biochem., 268, 3974, 2001) and having the nucleotide sequence of SEQ ID NO: 3 was amplified through PCR by using, as a template, genomic DNA extracted from *Bacillus* sp. KSM-K38 strain (FERM BP-6946), and a primer set (K38matu-F2 (ALAA) and SP64K38-R (XbaI)) shown in Table 1. Also, a 0.6 kb DNA fragment (I) including the transcription initiation regulatory region, translation initiation regulatory region, and secretion-signal-sequence-encoding region of an alkaline cellulase gene (JP-A-2000-210081) was amplified through PCR by using, as a template, genomic DNA extracted from *Bacillus* sp. KSM-S237 strain (FERM BP-7875), and a primer set (S237 ppp-F2 (BamHI) and S237 ppp-R2 (ALAA)) shown in Table 1.

Subsequently, SOE-PCR was carried out by use of the thus-prepared two fragments (H) and (I) in combination as templates, and by use of a primer set (S237 ppp-F2 (BamHI) and SP64K38-R (XbaI)) shown in Table 1, to thereby yield a 20.1 kb DNA fragment (J) in which the alkaline amylase gene was ligated to the downstream of the transcription initiation regulatory region, translation initiation regulatory region, and secretion-signal-sequence-encoding region of the alkaline cellulase gene. The thus-obtained 2.2 kb DNA fragment (J) was inserted into the restriction enzyme BamHI-XbaI cleavage site of a shuttle vector pHY300PLK (product of Yakult), to thereby construct a plasmid pHYK38(S237ps) for evaluation of alkaline amylase productivity.

The plasmid pHYK38(S237ps) for evaluation of alkaline amylase productivity was introduced into the prsA-Ka strain obtained in Example 1 and *Bacillus subtilis* 168 strain as control through the protoplast transformation method. Cells of each of the resultant strains were shake-cultured in an LB medium (10 mL) at 37° C. overnight. The resultant culture liquid (0.05 mL) was inoculated into a 2×L-maltose medium (50 mL) containing 15 ppm tetracycline, followed by shake culturing at 30° C. for five days.

After completion of culturing, cells were removed through centrifugation, and the alkaline amylase activity in the culture supernatant was determined, to thereby calculate the amount of alkaline amylase extracellularly secreted from the cells during culturing. The amylase activity in the culture supernatant was determined by means of Liquitec Amy EPS (product of Roche Diagnostic). Specifically, an R1-R2 mixture (100 µL) (R1 (coupling enzyme):R2 (amylase substrate)=5:1 (vol.)) was added to and mixed with a sample solution (50 µL) appropriately diluted with 1% NaCl-1/7.5M phosphate buffer (pH 7.4, product of Wako Pure Chemical Industries, Ltd.), and the amount of p-nitrophenol released during reaction at 30° C. was quantitatively determined on the basis of a change in absorbance at 405 nm (OD 405 nm). The amount of enzyme required for release of 1 µmol of p-nitrophenol for one minute was defined as 1 U.

As is clear from the alkaline amylase data shown in Table 2, when the prsA-Ka strain is employed as a host, secretion/production of alkaline amylase is enhanced, as compared with the case where the control 168 strain (wild-type strain) is employed. Conceivably, this enhancement of alkaline amylase production results from an increase in secretion efficiency of the protein by virtue of enhancement of expression of the prsA gene in the prsA-Ka strain as compared with the case of the wild-type strain, and an increase in amount of PrsA protein on the cell membrane.

TABLE 2

| Strain name | Enhanced gene | Amount of secreted/produced alkaline amylase (relative value) |
|---|---|---|
| prsA-Ka strain | prsA | 537 |
| 168 strain | None | 100 |

Example 3

Substitution of abrB Gene in Genome with Drug-resistant Gene

Next will be described a method for substituting an abrB gene in the genome with a drug-resistant gene with reference to FIG. 3. The abrB gene encodes a transcription factor which plays an important role in controlling expression of various genes involved in, for example, sporulation, competence, or nutrition acquisition during the transition from logarithmic growth phase to stationary phase.

By using, as a template, genomic DNA extracted from *Bacillus subtilis* 168 strain, and a primer set (abrB-FW and abrB/Cm-R) shown in Table 1, a 1.0kb fragment (A) adjacent upstream to the abrB gene in the genome was amplified through PCR. Also, by using, as a template, the aforementioned genomic DNA, and a primer set (abrB/Cm-F and abrB-RV), a 1.0 kb fragment (B) adjacent downstream to the abrB gene in the genome was amplified through PCR.

In addition, by using, as a template, plasmid pC194 DNA, and a primer set (catf and catr) shown in Table 1, a 0.85 kb chloramphenicol (Cm)-resistant gene region (C) was prepared through PCR.

Subsequently, as shown in FIG. 3, SOE-PCR was carried out by use of the thus-obtained three fragments: the 1.0 kb fragment (A), the 1.0 kb fragment (B), and the Cm-resistant gene region (C) in combination as templates, and by use of a primer set (abrB-FW2 and abrB-RV2) shown in Table 1, to thereby prepare a 2.8 kb DNA fragment (D) including the 1.0 kb fragment (A), the Cm-resistant gene region (C), and the 1.0 kb fragment (B) in this sequence.

*Bacillus subtilis* 168 strain was transformed through the competent cell transformation method by use of the thus-obtained DNA fragment (D). Thereafter, colonies grown in an LB agar medium containing chloramphenicol (10 µg/mL) were separated as a transformant.

Genomic DNA was extracted from the resultant transformant, and substitution of the abrB gene with the Cm-resistant gene was confirmed through PCR.

Thus, an abrB gene-deleted strain (ΔabrB strain) was constructed. The aforementioned transformation procedure was repeated, except that *Bacillus subtilis* 168 strain was replaced with the prsA-Ka strain constructed in Example 1, to thereby construct a strain in which the abrB gene in the genome of the prsA-Ka strain was substituted with the Cm-resistant gene (prsAKΔabrB strain).

Example 4

Substitution of dltB Gene, dltD Gene, or dltABCDE Genes in Genome with Drug-resistant Gene In a manner similar to that described above in Example 3 in which substitution of the abrB gene with the drug-resistant gene had carried out, the dltB gene, the dltD gene, or the dltABCDE genes in the genome of *Bacillus subtilis* 168 strain were substituted with a chloramphenicol-resistant gene, to thereby construct a dltB gene-deleted strain (ΔdltB strain), a dltD gene-deleted strain (ΔdltD strain), and a dltABCDE genes-deleted strain (ΔdltA-E strain). These strains were constructed by use of primers shown in Table 1. Table 3 shows the primers employed for constructing the dlt gene-deleted strains and the ΔabrB strain. As has been known, the dltA, dltB, dltC, dltD, and dltE genes belong to the same operon, and these genes are involved in transformation of teichoic acid present in the cell wall and the cell membrane into teichuronic acid. Table 4 shows the functions of these genes.

TABLE 3

|  | For deletion of abrB gene | For deletion of dltB gene | For deletion of dltD gene | For deletion of dltA-E genes |
| --- | --- | --- | --- | --- |
| Amplification of fragment (A) | abrB-FW abrB/Cm-R | dltB-FW dltB/Cm-R | dltD-FW dltD/Cm-R | dltA-FW dltA/Cm-R |
| Amplification of fragment (B) | abrB/Cm-F abrB-RV | dltB/Cm-F dltB-RV | dltD/Cm-F dltD-RV | dltE/Cm-F dltE-RV |
| Amplification of fragment (C) | catf catr | catf catr | catf catr | catf catr |
| Amplification of fragment (D) | abrB-FW2 abrB-RV2 | dltB-FW2 dltB-RV2 | dltD-FW2 dltD-RV2 | dltA-FW2 dltE-RV2 |

TABLE 4

| Gene number | Gene name | Gene function, etc. |
| --- | --- | --- |
| BG10100 | abrB | Transcriptional regulator for genes induced in a transition period |
| BG10551 | dltA | D-alanine active enzyme (D-alanine-D-alanyl carrier protein ligase) |
| BG10550 | dltB | D-alanine transfer from D-alanine-D-alanyl carrier protein to undecaprenol phosphate |
| BG10549 | dltC | D-alanyl carrier protein |
| BG10548 | dltD | D-alanine transfer from undecaprenol phosphate to poly(glycerophosphate) chain |
| BG10547 | dltE | Involved in biosynthesis of lipoteichoic acid |

In a manner similar to that described above, the dltABCDE genes in the genome of the prsA-Ka strain constructed in Example 1 were substituted with a chloramphenicol-resistant gene, to thereby construct a prsAKΔdltA-E strain.

Example 5

Evaluation of Secretion/Production of Alkaline Amylase—2

The plasmid pHYK38(S237ps) for evaluation of alkaline amylase productivity was introduced into the strain constructed in Example 3 or 4. Cells of the resultant strain were shake-cultured in an LB medium (10 mL) at 37° C. overnight. The resultant culture liquid (0.05 mL) was inoculated into a CSL fermentation medium (50 mL) containing 15 ppm tetracycline, followed by shake culturing at 30° C. for five days.

For comparison, *Bacillus subtilis* 168 strain as control and the prsA-Ka strain constructed in Example 1 were also evaluated.

Figure 4:
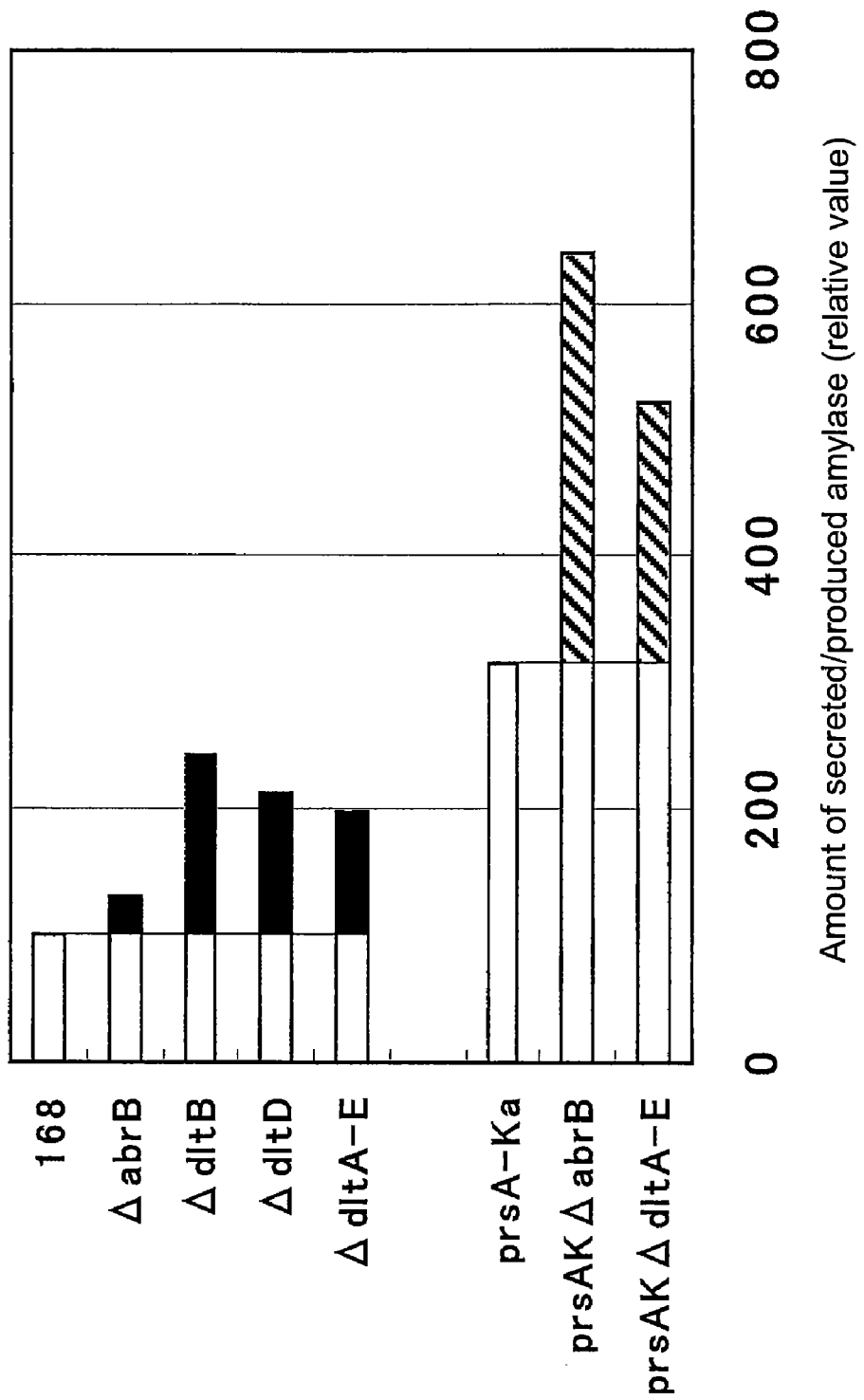
FIG. 4 is a graph showing alkaline amylase secretion-productivity of the microorganism of the present invention.

After completion of culturing, the alkaline amylase activity of culture supernatant was determined. As shown in FIG. 4, secretion/production of alkaline amylase was enhanced by the prsAKΔabrB strain and the prsAKΔdltA-E strain, as compared with the case of the prsA-Ka strain. In addition, an increase in amount of produced alkaline amylase by the prsAKΔabrB strain and the prsAKΔdltA-E strain with respect to the case of the prsA-Ka strain (corresponding to a hatched portion shown in FIG. 4) was more pronounced than an increase in amount of produced alkaline amylase by the ΔabrB strain, the ΔdltB strain, the ΔdltD strain, or the ΔdltA-E strain with respect to the case of *Bacillus subtilis* 168 strain (corresponding to a black portion shown in FIG. 4). These data suggest that, in the prsAKΔabrB strain and the prsAKΔdltA-E strain, enhancement of expression of the prsA gene and deletion of the given gene (genes) act synergistically on improvement of alkaline amylase productivity.

Example 6

Evaluation of the Effect of Combination of Enhancement of Expression of prsA Gene Derived from *Bacillus cereus* and Deletion of abrB Gene on Secretion/Production of Alkaline Amylase The prsA gene derived from *Bacillus cereus* (SEQ ID NO: 55) is a gene corresponding to the prsA gene of *Bacillus subtilis*. In a manner similar to that described in Example 1, there was constructed a mutant strain in which expression of the prsA gene derived from *Bacillus cereus* was enhanced. Specifically, by using, as a template, genomic DNA extracted from *Bacillus cereus*, and a primer set (Bce/PVG-F and Bce/emf2-R) shown in Table 1, a 0.9 kb fragment (A) including the prsA gene derived from *Bacillus cereus* was amplified through PCR. By using, as a template, genomic DNA extracted from the prsA-Ka strain constructed in Example 1, and two primer sets (amyEfw2 and PVG-R, and emf2 and amyErv2) shown in Table 1, a 1.2 kb fragment (B) in which a region including the transcription initiation regulatory region and ribosome-binding site of the spoVG gene was ligated to the downstream of the 5'-side region of the amyE gene, and a 2.3 kb fragment (C) in which the 3'-side region of the amyE gene was ligated to the downstream of an erythromycin-resistant gene, were amplified through PCR.

Subsequently, SOE-PCR was carried out by use of the thus-obtained three fragments (A), (B), and (C) in combination as templates, and by use of a primer set (amyEfw1 and amyErv1) shown in Table 1, to thereby prepare a DNA fragment (D) (total length of 4.3 kb), in which the three fragments (B), (A), and (C) were ligated in this sequence; and the gene fragment, in which the prsA gene derived from *Bacillus* cereus was ligated to the downstream of the transcription initiation regulatory region and ribosome-binding site of the spoVG gene and the erythromycin-resistant gene was ligated to the downstream of the prsA gene, was inserted into the center of the amyE gene. Bacillus subtilis 168 strain was transformed by use of the thus-obtained 4.3 kb DNA fragment (D), to thereby construct a prsAbc-K strain.

Subsequently, in a manner similar to that described in Example 3, the abrB gene in the genome of the prsAbc-K strain was substituted with a chloramphenicol-resistant gene, to thereby construct a prsAbcKΔabrB strain.

In a manner similar to that described in Example 2, the above-constructed prsAbc-K strain and prsAbcKΔabrB strain were subjected to evaluation of secretion/production of alkaline amylase. For comparison, Bacillus subtilis 168 strain as control and the ΔabrB strain were also evaluated.

Figure 5:
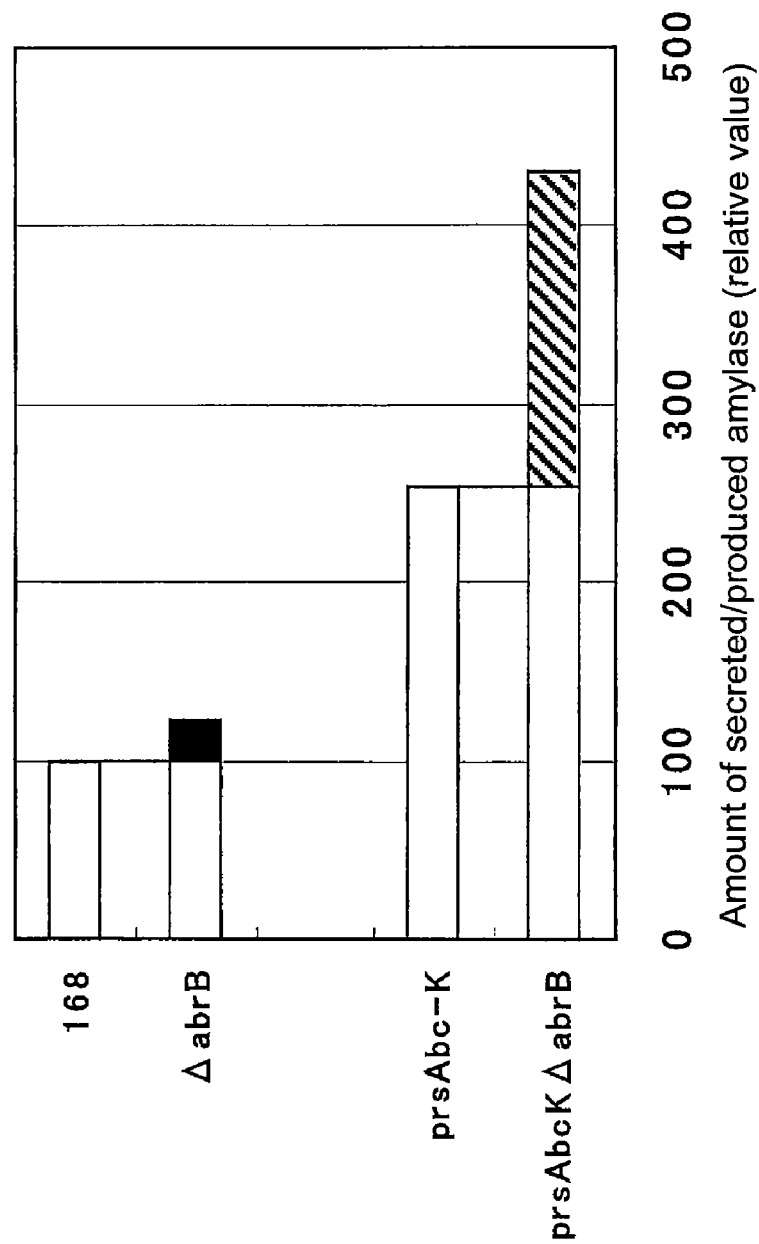
FIG. 5 is a graph showing alkaline amylase secretion-productivity of the microorganism of the present invention.

As shown in FIG. 5, secretion/production of alkaline amylase was considerably enhanced in the prsAbc-K strain, as compared with the case of Bacillus subtilis 168 strain. In addition, the strain prepared by deleting the abrB gene from the prsAbc-K strain exhibited further improved alkaline amylase productivity. These data suggest that, similar to the case described in Example 5, enhancement of expression of the prsA gene derived from Bacillus cereus and deletion of the abrB gene act synergistically on improvement of alkaline amylase productivity. This indicates that employment of a gene corresponding to the Bacillus subtilis prsA gene provides effects comparable to those obtained in the case where the Bacillus subtilis prsA gene is employed.

What is claimed is:

1. A recombinant microorganism produced by transferring a gene encoding a protein or polypeptide of interest to a microorganism strain, wherein the recombinant microorganism is prepared by:

inserting, into the genome of a parental microorganism, [i] a transcription initiation regulatory region or [ii] both the transcription initiation regulatory region and a ribosome-binding site, such that said [i] or [ii] is operably linked to the upstream of a Bacillus subtilis prsA gene or prsA gene that encodes a polypeptide with chaperone activity, thereby enhancing the expression of said prsA gene, wherein said transcription initiation regulatory region is not the original transcription initiation regulatory region of said prsA gene, or inserting, into the genome of a parental microorganism, a gene fragment prepared by operably linking a transcription initiation regulatory region or both the transcription initiation regulatory region and a ribosome-binding site to the upstream of the Bacillus subtilis prsA gene or a prsA gene that encodes a polypeptide with chaperone activity, thereby enhancing the expression of said prsA gene, wherein said transcription initiation regulatory region is not the original transcription initiation regulatory region of said prsA gene; and deleting or inactivating one or more genes selected from the group consisting of an abrB gene, a dltA gene, a dltB gene, a dltC gene, a dltD gene, and a dltE gene.

2. The recombinant microorganism according to claim 1, wherein the transcription initiation regulatory region that functions in the microorganism, or both the transcription initiation regulatory region and the ribosome-binding site that function in the microorganism, are derived from a Bacillus subtilis spoVG gene.

3. The recombinant microorganism according to claim 1, wherein the abrB gene is deleted or inactivated.

4. The recombinant microorganism according to claim 1, wherein the dltB gene, the dltD gene, or the dltABCDE genes are deleted or inactivated.

5. The recombinant microorganism according to claim 1, wherein the parental microorganism is a bacterium belonging to the genus Bacillus.

6. The recombinant microorganism according to claim 5, wherein the bacterium belonging to the genus Bacillus is Bacillus subtilis.

7. The recombinant microorganism according to claim 1, wherein one or more regions selected from the group consisting of a transcription initiation regulatory region, a translation initiation regulatory region, and a secretion signal region are ligated to the upstream of a gene encoding a protein or polypeptide of interest.

8. The recombinant microorganism according to claim 7, wherein the following three regions: the transcription initiation regulatory region; the translation initiation regulatory region; and the secretion signal region are ligated to the upstream of the gene encoding the protein or polypeptide of interest.

9. The recombinant microorganism according to claim 7, wherein the secretion signal region is derived from a cellulase gene of a bacterium belonging to the genus Bacillus, and the transcription initiation regulatory region and the translation initiation regulatory region are derived from a 0.6 to 1 kb region upstream of the cellulase gene.

10. The recombinant microorganism according to claim 7, wherein the following three regions: the transcription initiation regulatory region; the translation initiation regulatory region; and the secretion signal region are selected from the group consisting of (a) a DNA fragment consisting of a nucleotide sequence as set forth in nucleotide numbers 1 to 659 of SEQ ID NO: 5, (b) a DNA fragment consisting of a nucleotide sequence as set forth in nucleotide numbers 1 to 696 of SEQ ID NO: 7, (c) a DNA fragment consisting of a nucleotide sequence having an identity of 70% or higher to a nucleotide sequence of any one of the DNA fragments of (a) or (b), and (d) a DNA fragment consisting of a nucleotide sequence obtained by partial deletion of a nucleotide sequence of any one of the DNA fragments of (a) or (b).

11. A method for producing a protein or polypeptide of interest, comprising employing the recombinant microorganism as recited in any one of claims 1 to 10.

* * * * *